United States Patent
Ojima et al.

(10) Patent No.: US 12,018,003 B2
(45) Date of Patent: Jun. 25, 2024

(54) SUBSTITUTED PYRIMIDINES AS MATRIX METALLOPROTEINASE-9 HEMOPEXIN DOMAIN INHIBITORS

(71) Applicant: The Research Foundation for The State University of New York, Albany, NY (US)

(72) Inventors: Iwao Ojima, Port Jefferson, NY (US); Vincent Alford, Sunnyvale, CA (US); Anushree Kamath, Issaquah, WA (US); Jian Cao, S. Setauket, NY (US); Xiadong Ren, Port Jefferson Station, NY (US); Nicole Sampson, Setauket, NY (US); Monaf Awwa, Bel Air, MD (US)

(73) Assignee: The Research Foundation for The State University of New York, Albany, NY (US)

( * ) Notice: Subject to any disclaimer, the term of this patent is extended or adjusted under 35 U.S.C. 154(b) by 116 days.

(21) Appl. No.: 17/353,075

(22) Filed: Jun. 21, 2021

(65) Prior Publication Data
US 2021/0309616 A1 Oct. 7, 2021

Related U.S. Application Data

(62) Division of application No. 16/494,984, filed as application No. PCT/US2018/023676 on Mar. 22, 2018, now Pat. No. 11,040,947.

(60) Provisional application No. 62/474,905, filed on Mar. 22, 2017, provisional application No. 62/526,703, filed on Jun. 29, 2017.

(51) Int. Cl.
| | | |
|---|---|---|
| C07D 487/04 | (2006.01) | |
| A61P 35/00 | (2006.01) | |
| C07D 239/56 | (2006.01) | |
| C07D 239/95 | (2006.01) | |
| C07D 403/12 | (2006.01) | |

(52) U.S. Cl.
CPC ............ *C07D 239/95* (2013.01); *A61P 35/00* (2018.01); *C07D 239/56* (2013.01); *C07D 403/12* (2013.01)

(58) Field of Classification Search
CPC .................................................... C07D 487/04
USPC ......................................................... 544/319
See application file for complete search history.

(56) References Cited

U.S. PATENT DOCUMENTS

| | | |
|---|---|---|
| 4,536,335 A | 8/1985 | Kim et al. |
| 4,640,799 A | 2/1987 | Kim et al. |
| 4,665,170 A | 5/1987 | Kim et al. |
| 5,393,762 A | 2/1995 | Desai et al. |
| 5,519,033 A | 5/1996 | Rosen et al. |
| 5,750,535 A | 5/1998 | Clancy |
| 5,952,320 A | 9/1999 | Davidsen et al. |
| 5,955,474 A | 9/1999 | Croci |
| 6,194,436 B1 | 2/2001 | Howard |
| 6,376,507 B1 | 4/2002 | Nelson et al. |
| 6,777,424 B2 | 8/2004 | Littman |
| 7,018,999 B2 | 3/2006 | Aimone et al. |
| 7,312,219 B2 | 12/2007 | Dang et al. |
| 7,317,031 B2 | 1/2008 | Lin et al. |
| 7,335,653 B2 | 2/2008 | Ungashe et al. |
| 7,351,738 B2 | 4/2008 | Pulley et al. |
| 7,429,618 B2 | 9/2008 | Gouliaev et al. |
| 7,666,855 B2 | 2/2010 | Reddy et al. |
| 7,923,556 B2 | 4/2011 | Wrobleski et al. |
| 8,148,363 B2 | 4/2012 | Clasby et al. |
| 8,236,809 B2 | 8/2012 | Tegtmeier et al. |
| 8,415,321 B2 | 4/2013 | Schinazi et al. |
| 8,501,812 B2 | 8/2013 | Davis et al. |
| 8,791,137 B2 | 7/2014 | Zhou et al. |
| 8,937,041 B2 | 1/2015 | McDaniel et al. |
| 9,040,498 B2 | 5/2015 | Lakshman |
| 9,834,521 B2 | 12/2017 | Zech et al. |
| 2012/0142742 A1 | 6/2012 | Riedl et al. |
| 2016/0039808 A1 | 2/2016 | Kanouni et al. |

FOREIGN PATENT DOCUMENTS

| | | | |
|---|---|---|---|
| GB | 587548 | * | 4/1947 |
| WO | WO2014036022 A1 | | 3/2014 |

OTHER PUBLICATIONS

International Search Report for corresponding International Application No. PCT/US2018/023676, pp. 1-5, dated Jul. 6, 2018.
Cain, Chris, "A Bid to Revive MMP Inhibitors," Science-Business exchange, vol. 4, pp. 701-701 (2011).
Dufour, Antoine, et al. "Small-Molecule Anticancer Compounds Selectively Target the Hemopexin Domain of Matrix Metalloproteinase-9," Cancer Research, vol. 71, No. 14, pp. 4977-4988 (2011).
Hallett, Miranda A., "The Treatment of Breast Cancer Tumor Growth and Metastasis with an Anti-MMP9 DNAzyme," The University of Tennessee Health Science Center (2011).

* cited by examiner

*Primary Examiner* — Douglas M Willis
(74) *Attorney, Agent, or Firm* — Hoffmann & Baron LLP

(57) ABSTRACT

The invention relates to substituted pyrimidine compounds with the following formula:

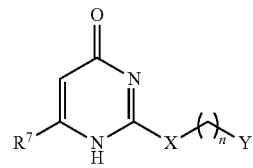

or a pharmaceutically acceptable salt, stereoisomer, or tautomer thereof. These compounds selectively target the hemopexin domain of matrix metalloproteinase 9 (MMP-9) and do not inhibit the protease's catalytic functions. The invention also relates to methods of treating cancer in a patient in need thereof with the compounds.

5 Claims, No Drawings

SUBSTITUTED PYRIMIDINES AS MATRIX METALLOPROTEINASE-9 HEMOPEXIN DOMAIN INHIBITORS

CROSS REFERENCE TO RELATED APPLICATIONS

This application is a divisional of U.S. patent application Ser. No. 16/494,984, filed on Sep. 17, 2019, which is the U.S. National Phase of, and Applicant claims priority from, PCT/US2018/23676, filed on Mar. 22, 2018, which claims priority from U.S. Provisional Application No. 62/474,905, filed on Mar. 22, 2017, and U.S. Provisional Application No. 62/526,703, filed on Jun. 29, 2017, the contents of which are herein incorporated by reference in their entireties.

This invention was made with government support under CA166936 awarded by the National Institutes of Health. The government has certain rights in the invention.

BACKGROUND OF THE INVENTION

Matrix metalloproteinase 9 (MMP-9) is a secreted type IV collagenase known for its role in multiple pathological processes associated with cancer progression. Compounds that inhibit MMP-9's proteolytic function have had little success due to lack of inhibitor specificity. DNA sequence analysis and structural mutagenesis of proMMP-9 led to the identification of the hemopexin domain as a unique and required domain for interaction with CD44. This interaction at the cell surface results in enhanced cancer cell migration through activation of MAP kinase dependent signaling. The data indicate that proMMPs have a role in potentiating signaling cascades involved in cancer progression independent of catalytic activity, and a small molecule inhibitor can specifically block this process.

There is a need to discover more potent MMP-9 inhibitors which may be evaluated for their binding affinity ($K_d$) for MMP-9s hemopexin domain in addition to testing their ability to inhibit proMMP9-mediated migration using a cell based 2-D collagen dot migration assay. Furthermore, these compounds must selectively target the hemopexin domain of MMP-9 and not inhibit the protease's catalytic functions. Such compounds may have application as cancer treatment drugs for various cancers including chronic lymphocytic leukemia and refractory lymphomas.

SUMMARY OF THE INVENTION

One aspect of the invention relates to a compound of Formula I:

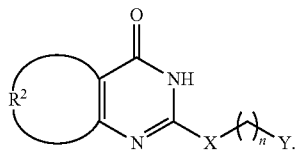

wherein:
Y is —$CONHR^1$ or —$NHCOR^1$;
$R^1$ is alkyl, cycloalkyl, or aryl;
$R^2$ is a substituted or unsubstituted 5, 6, 7, or 8-membered carbocyclic or heterocyclic ring containing at least one double bond;
X is S, NH, $NR^3$, or O;
$R^3$ is $C_{1-5}$ alkyl; and
n is 2, 3, or 4, with the proviso that n 2 when Y is —$CONHR^1$;

alkyl groups are branched or unbranched, saturated or unsaturated, and have 1-18 carbon atoms in their longest chain;

cycloalkyl groups are carbocyclic or heterocyclic, fused or unfused, non-aromatic ring systems having a total of 5-16 ring members including carbonyls and substituent rings;

aryl groups are carbocyclic or heterocyclic;

carbocyclic aryl groups are fused or unfused ring systems having a total of 6-16 ring members including substituent rings;

heterocyclic aryl groups are fused or unfused ring systems having a total of 5-16 ring members including substituent rings;

each alkyl, cycloalkyl, and aryl, independently, may be unsubstituted or substituted with one or more substituent at any position, with the proviso that phenyl groups are not 2,6-disubstituted;

alkyl substituents are halo, hydroxyl, $OR^4$, $SR^4$, $S(O)R^4$, $S(O)_2R^4$, $NH_2$, $NHR^4$, $NR^5R^6$, $NHCOR^4$, $NHCO_2R^4$, cycloalkyl, or aryl;

cycloalkyl substituents are halo, hydroxyl, $OR^4$, $SR^4$, $NH_2$, $NHR^4$, $NR^5R^6$, $NHCOR^4$, $NHCO_2R^4$, alkyl, cycloalkyl, or aryl;

aryl substituents are halo, hydroxyl, $OR^4$, $SR^4$, $NH_2$, $NHR^4$, $NR^5R^6$, $NHCO_2R^4$, CN, alkyl, cycloalkyl, aryl, nitro, $R^4CO$, carboxyl, $CO_2R^4$, $CONHR^4$, or $CONR^5R^6$; $R^4$, $R^5$, and $R^6$ are independently alkyl, cycloalkyl, or aryl;

$R^5$ and $R^6$ independently, may be combined to represent a heterocyclic alkyl or a heterocyclic aryl;

heterocyclic alkyl and heterocyclic aryl have at least one heteroatom selected from oxygen, nitrogen and sulfur; and halo substituents are fluoro, chloro, bromo, or iodo.

Another aspect of the invention relates to a compound of Formula II:

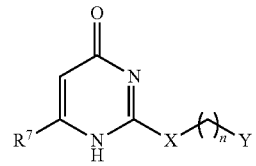

wherein:
Y is —$CONHR^1$ or —$NHCOR^1$;
$R^1$ is alkyl, cycloalkyl, or aryl;
X is S, NH, $NR^3$, or O;
$R^3$ is $C_{1-5}$ alkyl;
$R^7$ is $C_{1-6}$ alkyl; and
n is 2, 3, or 4, with the proviso that n 2 when Y is —$CONHR^1$;

alkyl groups are branched or unbranched, saturated or unsaturated, and have 1-18 carbon atoms in their longest chain;

cycloalkyl groups are carbocyclic or heterocyclic, fused or unfused, non-aromatic ring systems having a total of 5-16 ring members including carbonyls and substituent rings;

aryl groups are carbocyclic or heterocyclic;

carbocyclic aryl groups are fused or unfused ring systems having a total of 6-16 ring members including substituent rings;

heterocyclic aryl groups are fused or unfused ring systems having a total of 5-16 ring members including substituent rings;

each alkyl, cycloalkyl, and aryl, independently, may be unsubstituted or substituted with one or more substituent at any position;

alkyl substituents are halo, hydroxyl, $OR^4$, $SR^4$, $S(O)R^4$, $S(O)_2R^4$, $NH_2$, $NHR^4$, $NR^5R^6$, $NHCOR^4$, $NHCO_2R^4$, cycloalkyl, or aryl;

cycloalkyl substituents are halo, hydroxyl, $OR^4$, $SR^4$, $NH_2$, $NHR^4$, $NR^5R^6$, $NHCOR^4$, $NHCO_2R^4$, alkyl, cycloalkyl, or aryl;

aryl substituents are halo, hydroxyl, $OR^4$, $SR^4$, $NH_2$, $NHR^4$, $NR^5R^6$, $NHCO_2R^4$, CN, alkyl, cycloalkyl, aryl, nitro, $R^4CO$, carboxyl, $CO_2R^4$, $CONHR^4$, or $CONR^5R^6$;

$R^4$, $R^5$, and $R^6$ are independently alkyl, cycloalkyl, or aryl;

$R^5$ and $R^6$ independently, may be combined to represent a heterocyclic alkyl or a heterocyclic aryl;

heterocyclic alkyl and heterocyclic aryl have at least one heteroatom selected from oxygen, nitrogen and sulfur; and halo substituents are fluoro, chloro, bromo, or iodo.

The invention also relates to a method of treating cancer in a patient in need thereof, comprising administering a therapeutically effective amount of one or more compound of Formula I, Formula II, or a pharmaceutically acceptable salt thereof.

DETAILED DESCRIPTION OF THE INVENTION

The invention relates to novel MMP-9 hemopexin domain inhibitors. These compounds were formulated to be used to treat cancer patients.

In one embodiment, the invention relates to a compound of Formula I below:

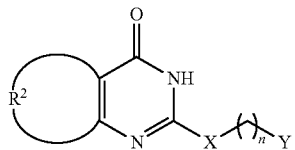

Formula I

In Formula I, Y is an amide of the following structure:

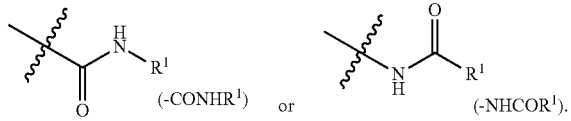

(-CONHR¹)   or   (-NHCOR¹).

The letter n denotes the length of the —CH2- chain which links X and Y. In general, n may be 2, 3, or 4, i.e., ethyl, propyl, or butyl chains. However, when Y is —CONHR¹, then n may not be 2. In other words, when Y is —CONHR¹, n is a propyl or butyl chain. When Y is —NHCOR¹, then n may be 2, 3, or 4. In a preferred embodiment, n is 3.

$R^1$ is alkyl, cycloalkyl, or aryl. Preferably, $R^1$ is substituted or unsubstituted phenyl or substituted or unsubstituted benzimidazolyl.

X is S, NH, $NR^3$, or O. Preferably, X is S. $R^3$ is $C_{1-5}$ alkyl. A $C_{1-5}$ alkyl is methyl, ethyl, propyl, butyl, and pentyl.

$R^2$ is a substituted or unsubstituted 5, 6, 7, or 8-membered carbocyclic or heterocyclic ring containing at least one double bond. One double bond is present where $R^2$ is fused to the other ring structure of Formula I. Substituents of the 5, 6, 7, or 8-membered carbocyclic or heterocyclic ring are the same as the cycloalkyl substituents described below. $R^2$ is preferably an unsubstituted, 6-membered ring.

Examples of $R^2$ include, but are not limited to, the following:

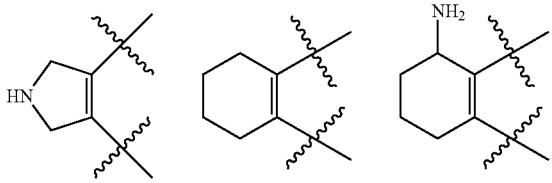

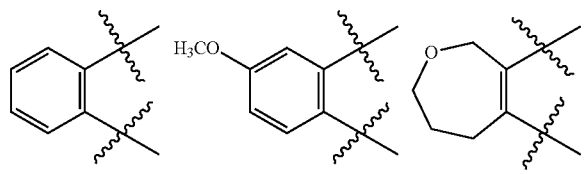

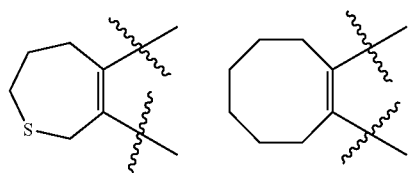

Preferably, $R^2$ is

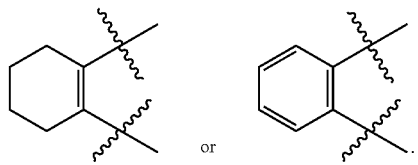 [SMILES: *C1=C(*)CCCC1 ; *c1ccccc1*]

For example, when $R^2$ is

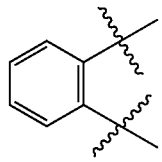 [SMILES: *c1ccccc1*]

the resulting compound is

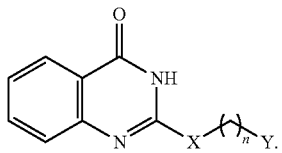

Alkyl groups are branched or unbranched, saturated or unsaturated, and have 1-18 carbon atoms in their longest chain, unless otherwise specified. Some examples of suitable straight-chained, saturated alkyl groups include methyl, ethyl, n-propyl, n-butyl, n-pentyl, n-hexyl groups and dodecyl and hexadecyl. Preferred straight chain, saturated alkyl groups include methyl and ethyl.

Some examples of suitable branched, saturated alkyl groups include isopropyl, isobutyl, sec-butyl, t-butyl, 1-methylbutyl, 2-methylbutyl, 3-methylbutyl (isopentyl), 1,1-dimethylpropyl, 1,2-dimethylpropyl, 2,2-dimethylpropyl (neopentyl), 1-methylpentyl, 2-methylpentyl, 3-methylpentyl, 4-methylpentyl groups, and 2-methyl-5-ethyldecyl. Preferred branched, saturated alkyl groups include isopropyl and t-butyl.

Some examples of unsaturated alkyl groups include ethenyl, ethynyl, propenyl, propargyl, isopropenyl, crotyl, 1-hexenyl, and 1-octenyl.

Cycloalkyl groups are carbocyclic or heterocyclic, fused or unfused, non-aromatic ring systems having a total of 5-16 ring members including substituent rings. Ring systems are monocyclic, bicyclic, tricyclic, or tetracyclic and can be bridged or non-bridged.

Some examples of carbocyclic alkyl groups include cyclobutanyl, cyclopentanyl, cyclohexanyl, and cycloheptanyl. Examples of fused carbocyclic alkyl groups include indan-1-yl, indqn-2-yl. Bridged groups include bicyclo [2.2.1] heptane, bicycico [5.2.0] nonane, and bicyclo [5.2.0] nonane.

Some examples of heterocyclic alkyl groups include pyrrolidinyl, piperidinyl, piperazinyl, tetrahydrofuranyl, morpholinyl, and oxazolidinyl. Examples of fused heterocyclic alkyl groups include benzomorpholinyl, benzopyrrolidinyl, indolinyl, and benzopiperidinyl.

Aryl groups can be either carbocyclic or heterocyclic.

Carbocyclic aryl groups are fused or unfused ring systems having a total of 6-16 ring members including substituent rings. A preferred unfused carbocyclic aryl group is phenyl.

Some examples of fused carbocyclic aryl groups include naphthyl, phenanthryl, anthracenyl, triphenylenyl, chrysenyl, and pyrenyl.

Heterocyclic aryl groups are fused or unfused ring systems having a total of 5-16 ring members including substituent rings.

Some examples of unfused heterocyclic aryl groups include thiophenyl, furyl, pyrrolyl, pyrazolyl, imidazolyl, oxazolyl, thiazolyl, pyridinyl, pyridazinyl, pyrimidinyl, and pyrazinyl.

Some examples of fused heterocyclic aryl groups include purinyl, 1,4-diazanaphthalenyl, indolyl, isoindolyl, benzimidazolyl, 4,5-diazaphenanthrenyl, benzoxazolyl, quinolinyl, isoquinolinyl, and benzofuranyl.

Heterocyclic alkyl and heterocyclic aryl have at least one heteroatom. Heteroatoms are oxygen, nitrogen, and sulfur.

Each alkyl, cycloalkyl, and aryl, independently, may be unsubstituted or substituted with one or more substituent at any position with the exception that phenyl groups may not be 2,6-disubstituted. Alkyl substituents are halo, hydroxyl, $OR^4$, $SR^4$, $S(O)R^4$, $S(O)_2R^4$, $NH_2$, $NHR^4$, $NR^5R^6$, $NHCOR^4$, $NHCO_2R^4$, cycloalkyl, or aryl. Cycloalkyl substituents are halo, hydroxyl, $OR^4$, $SR^4$, $NH_2$, $NHR^4$, $NR^5R^6$, $NHCOR^4$, $NHCO_2R^4$, alkyl, cycloalkyl, or aryl. Aryl substituents are halo, hydroxyl, $OR^4$, $SR^4$, $NH_2$, $NHR^4$, $NR^5R^6$, $NHCO_2R^4$, CN, alkyl, cycloalkyl, aryl, nitro, $R^4CO$, carboxyl, $CO_2R^4$, $CONHR^4$, or $CONR^5R^6$.

$R^4$, $R^5$, and $R^6$, independently represent alkyl, cycloalkyl, or aryl. For example, $R^4$ may represent methyl and $R^5$ may represent phenyl.

$R^5$ and $R^6$ independently, may be combined to represent a heterocyclic alkyl or a heterocyclic aryl. For example, when the substituent is $NR^5R^6$ and $R^5$ and $R^6$ are combined to present a heterocyclic alkyl, the resulting substituent is

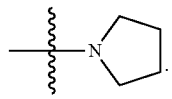

In another example, when the substituent is $CONR^5R^6$ and $R^5$ and $R^6$ are combined to represent a heterocyclic aryl, the resulting substituent may be

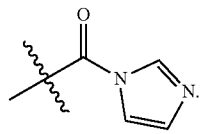 [SMILES: *C(=O)n1ccnc1]

Halo substituents are fluoro, chloro, bromo, or iodo. Preferred halo substituents are fluoro, chloro, or bromo.

Compounds according to Formula I when Y is —$CONHR^1$ include:

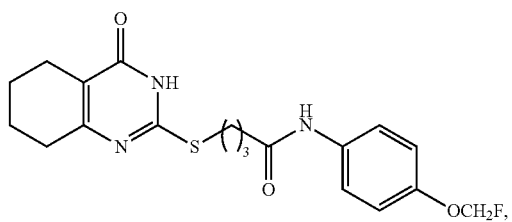

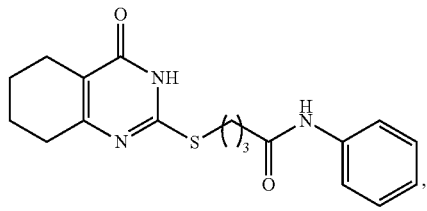

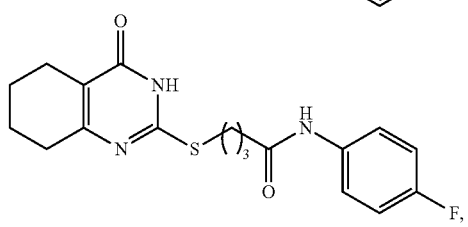

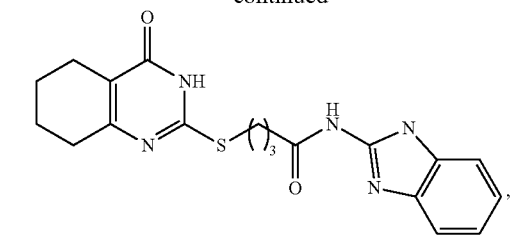
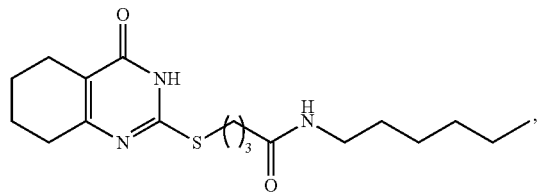
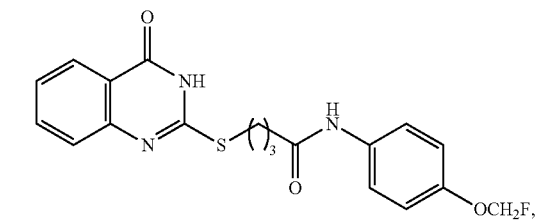
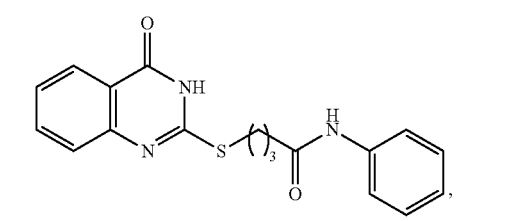
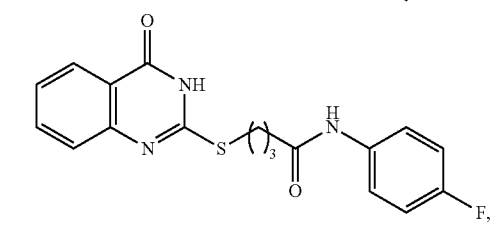
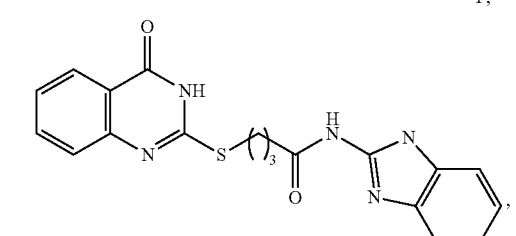
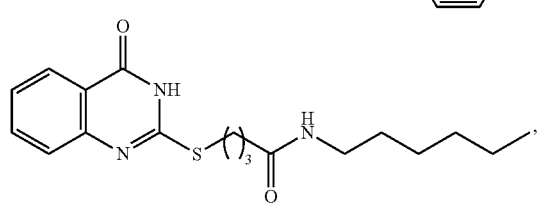
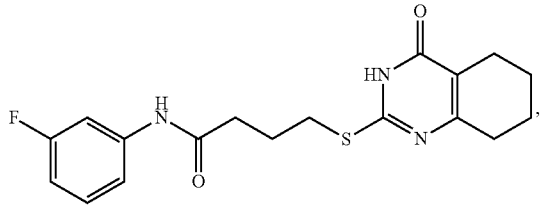
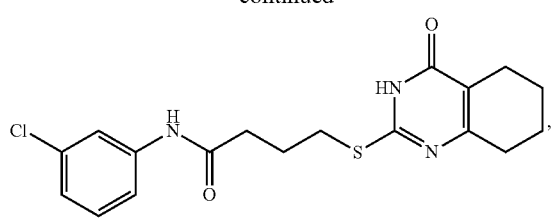
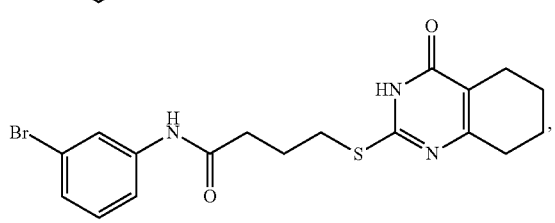
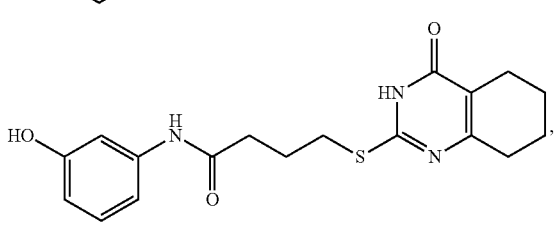
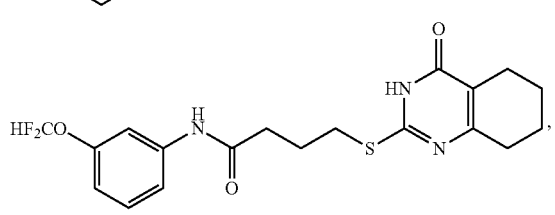
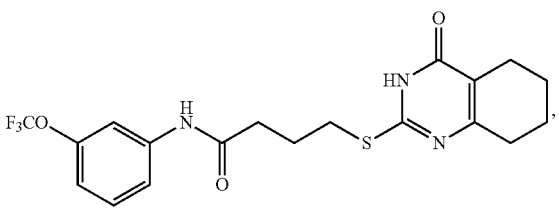
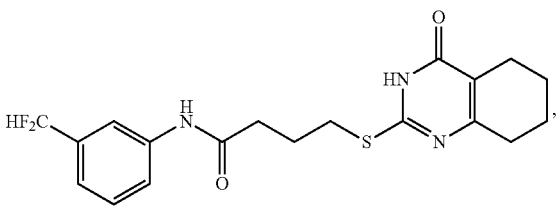
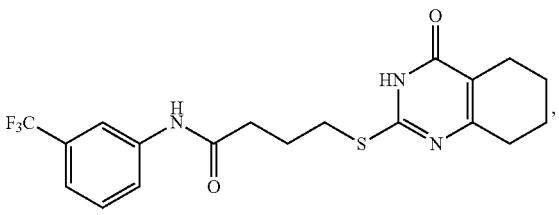
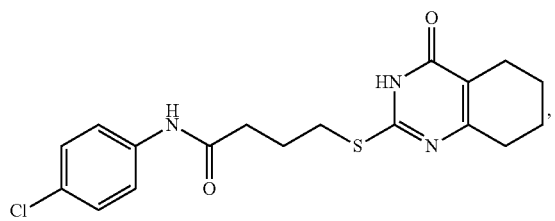

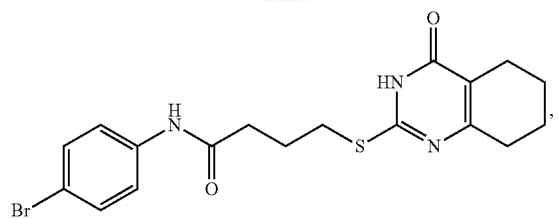
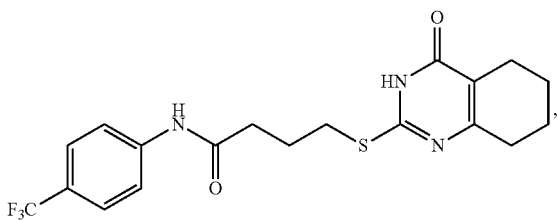
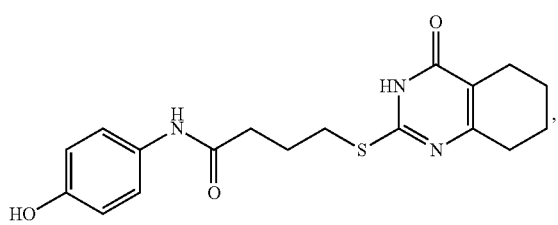
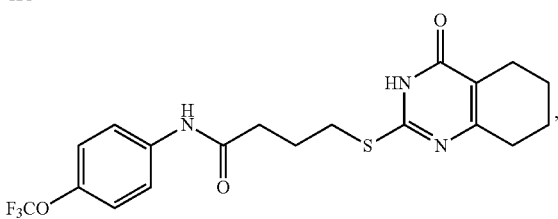
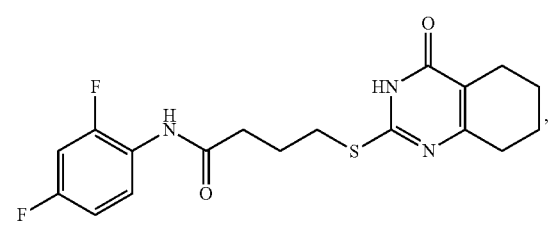
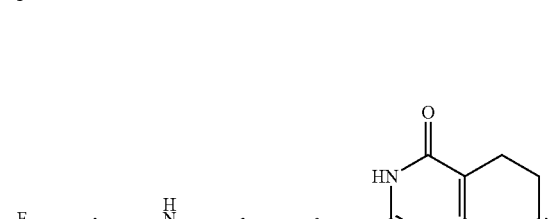
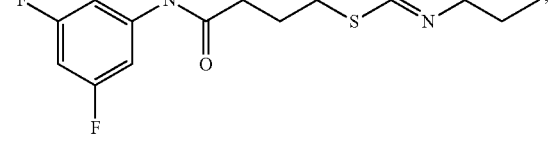
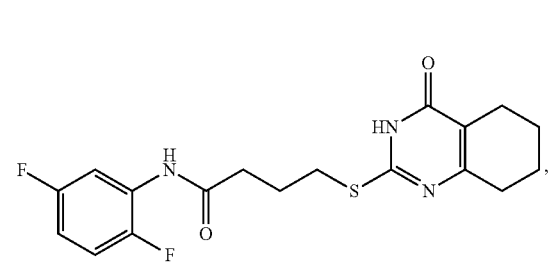
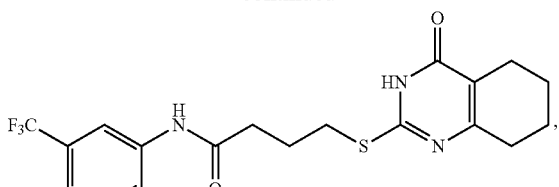
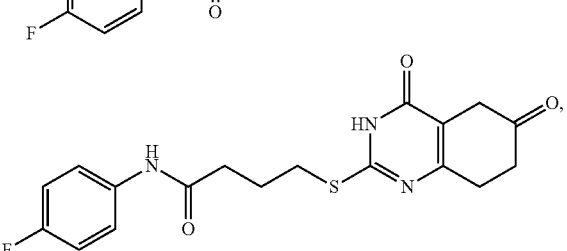
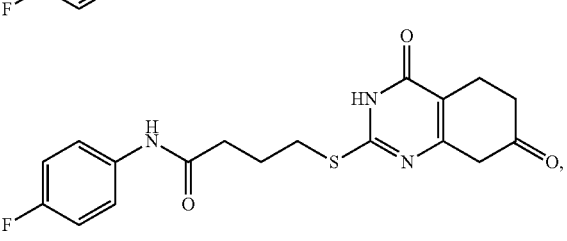
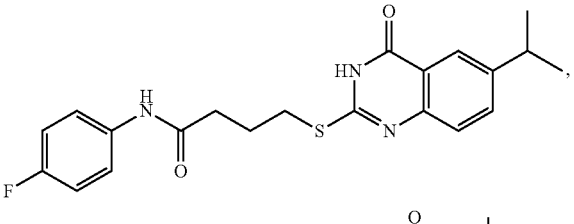
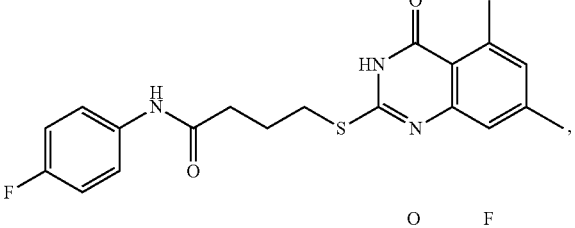
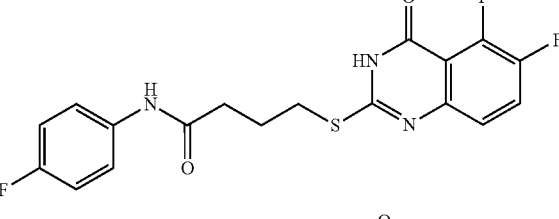
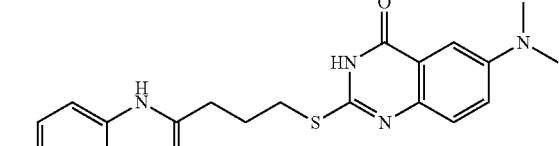
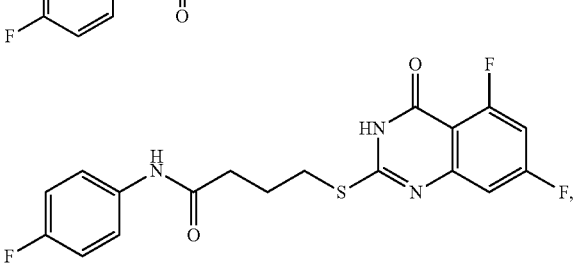

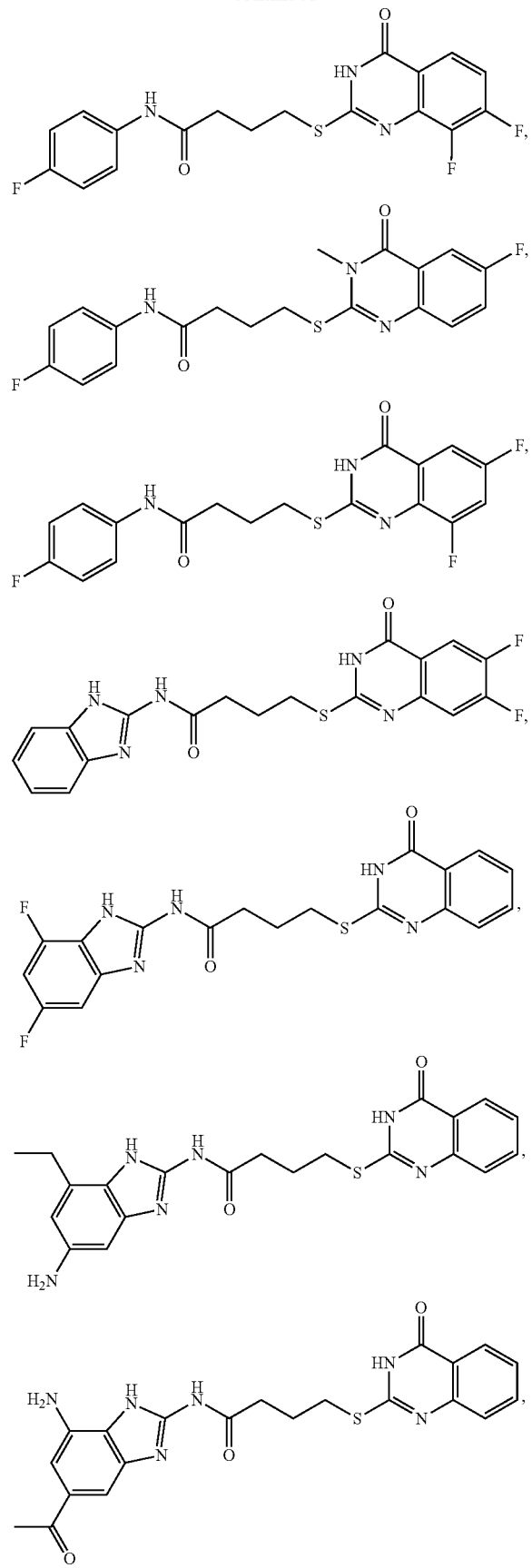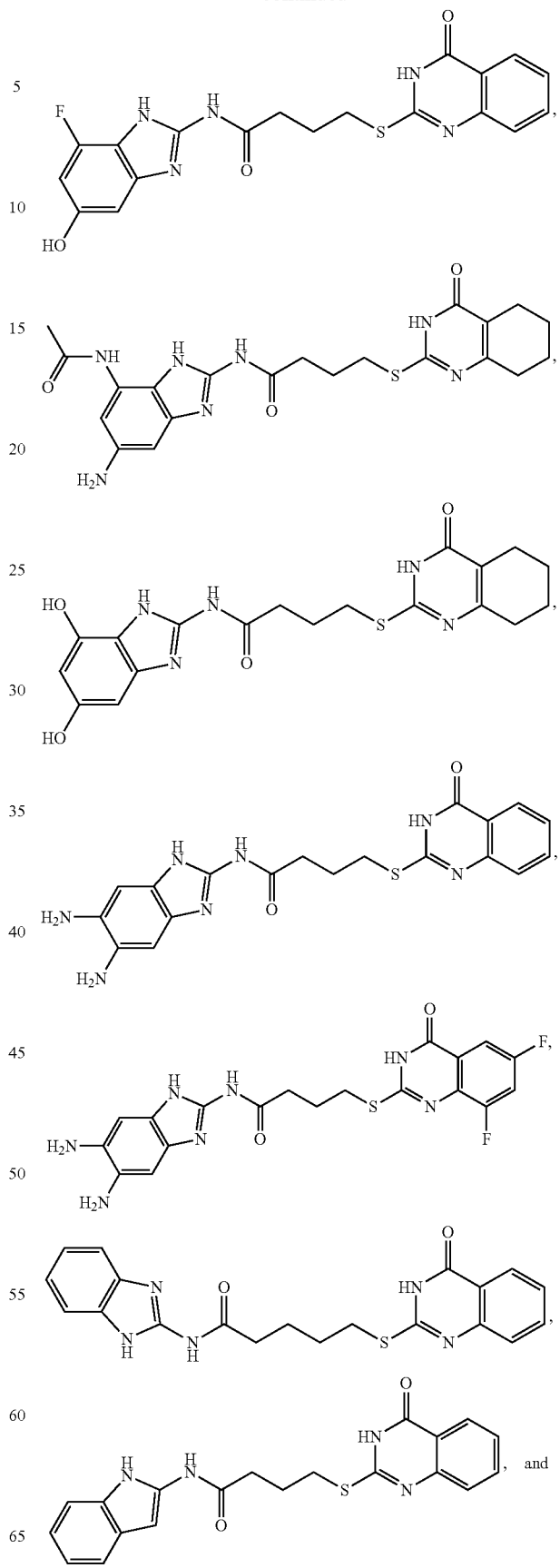

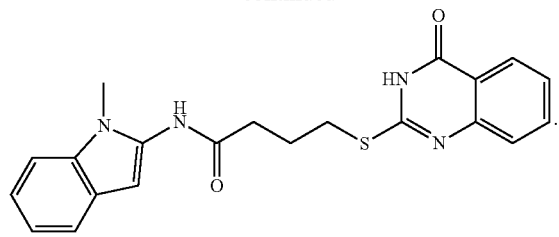
Compounds according to Formula I when Y is —NHCOR[1] include:
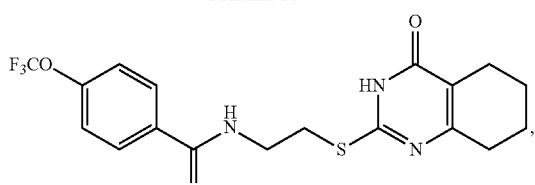
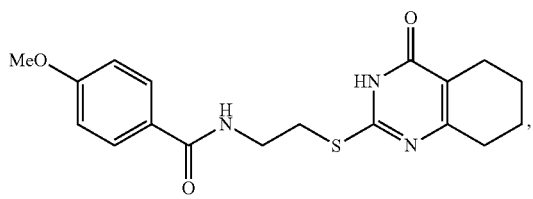
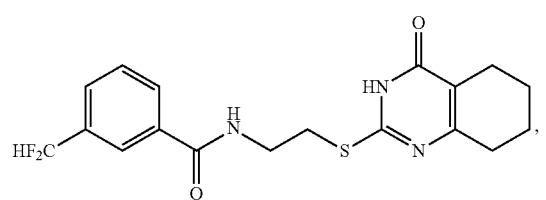
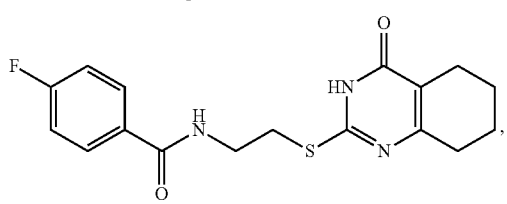
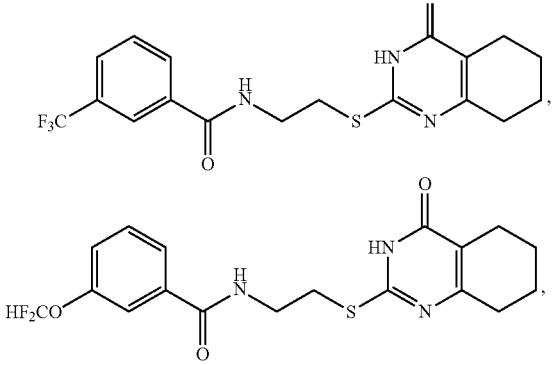
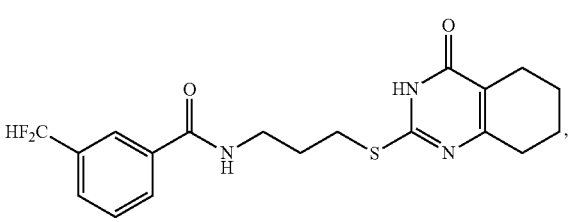
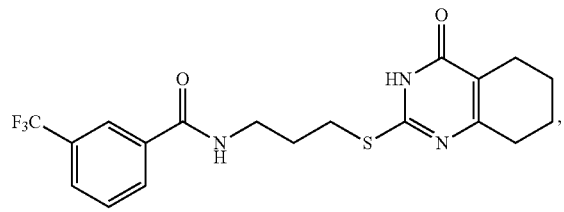
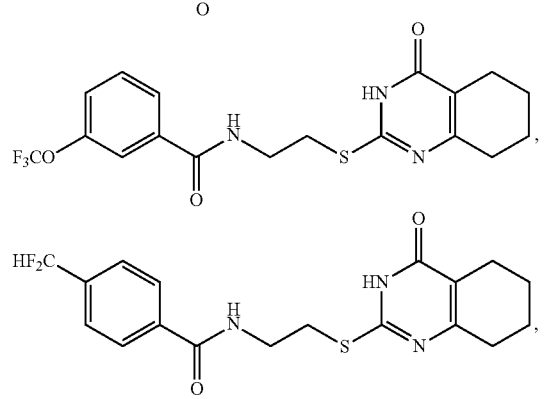
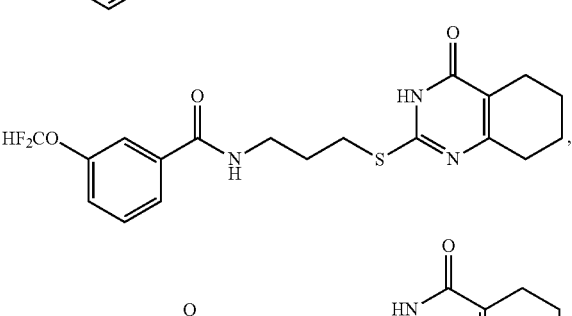
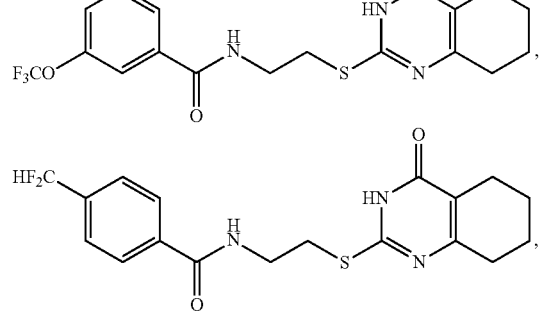
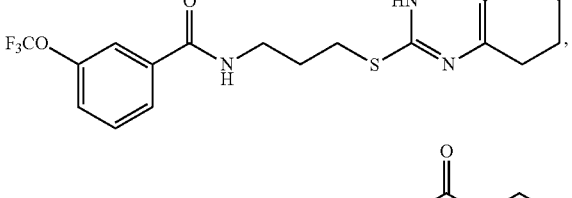
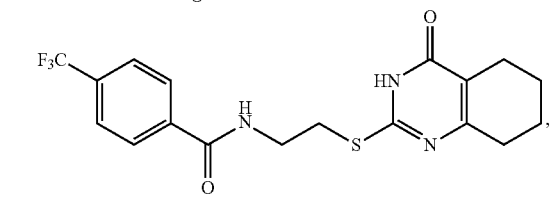
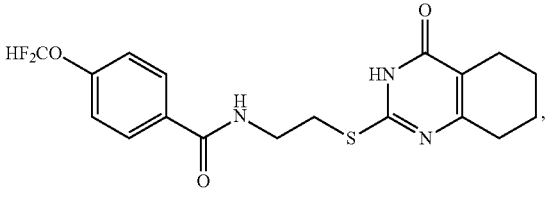

-continued
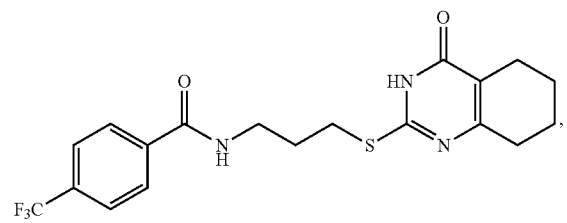
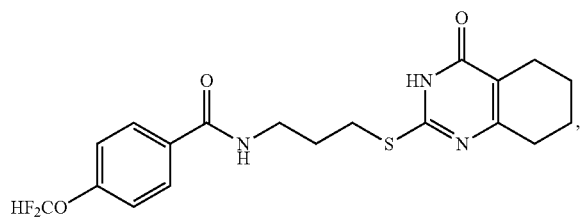
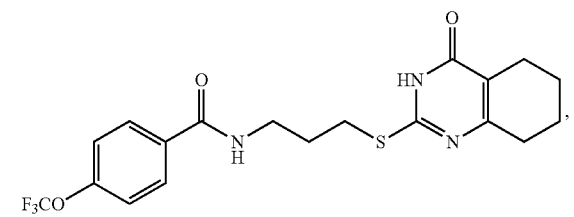
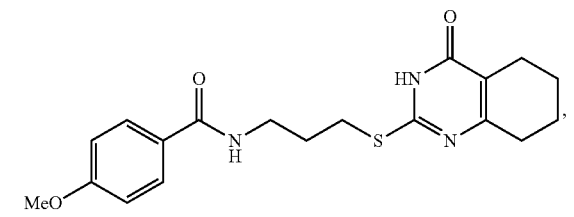
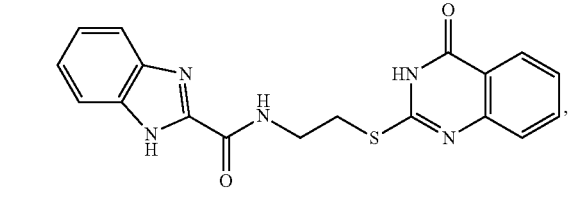
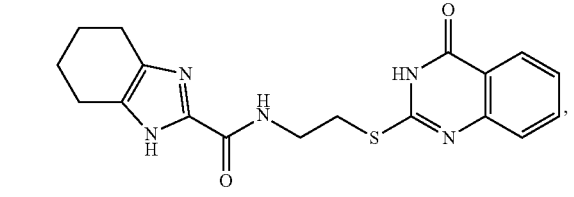
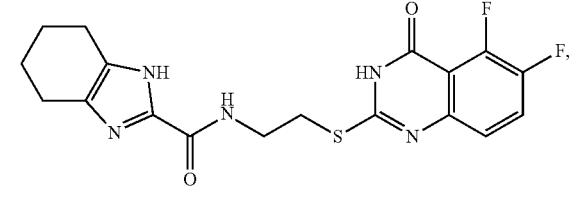
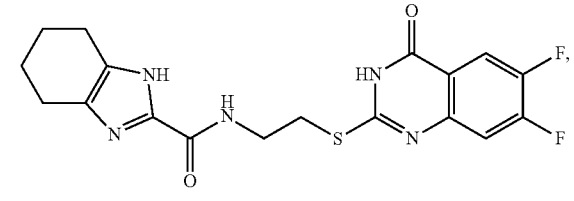
-continued
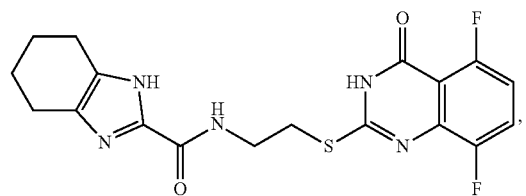
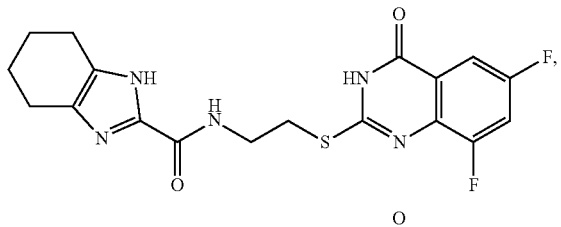
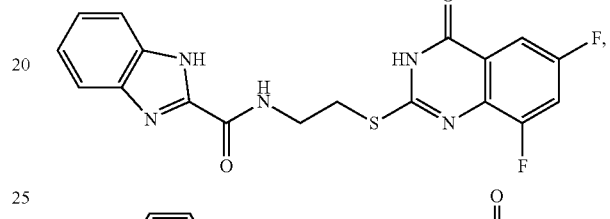
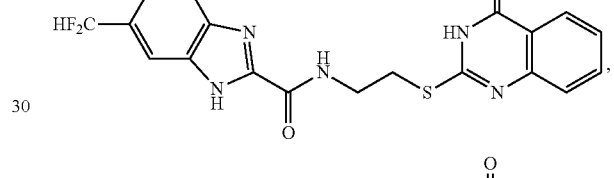
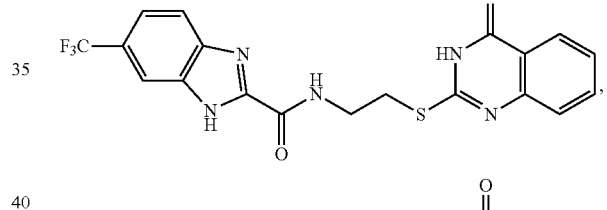
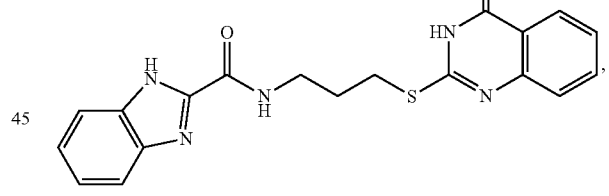
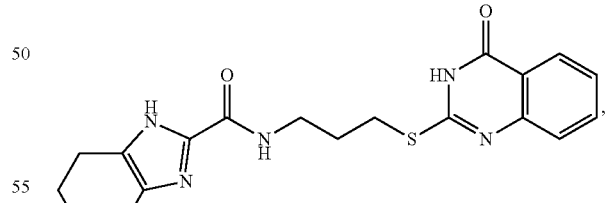
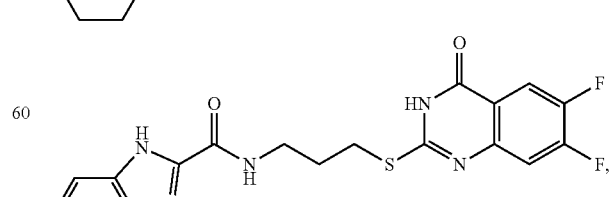

-continued

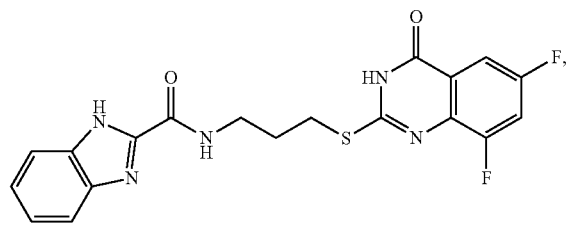

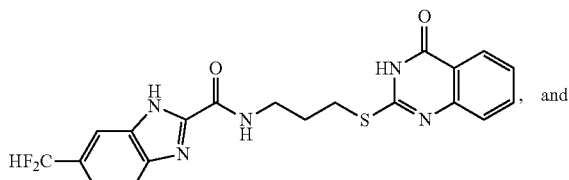
, and

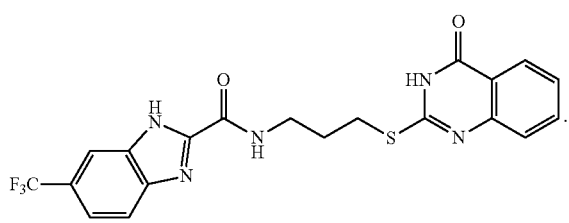
.

In another embodiment, the invention relates to compounds of Formula II shown below:

Formula II

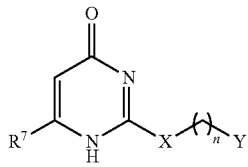

In Formula II, X, Y, and n are described above for Formula I. $R^7$ represents $C_{1-6}$ alkyl. $C_{1-6}$ alkyl includes methyl, ethyl, propyl, butyl, pentyl, and hexyl groups. $R^7$ is preferably propyl.

Compounds according to Formula II include, but are not limited to, the following:

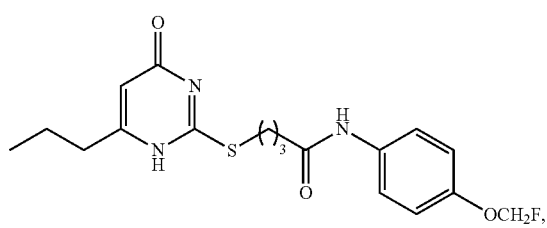
,

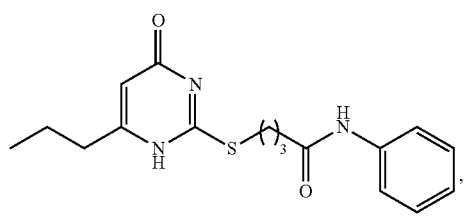
,

-continued

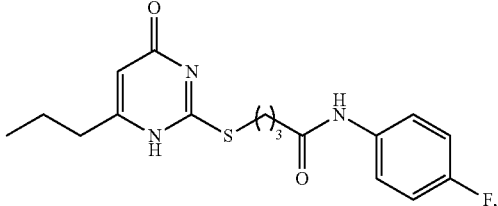
,

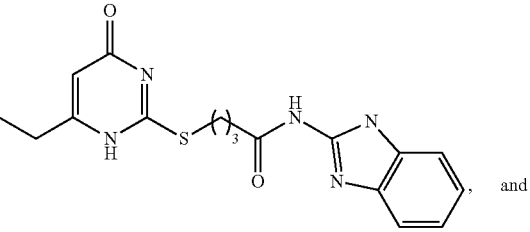
, and

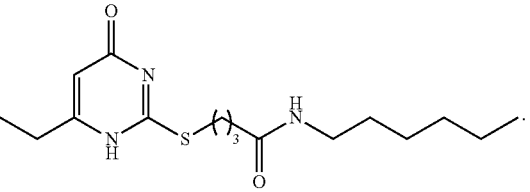
.

In this specification, groups of various parameters containing multiple members are described. Within a group of parameters, each member may be combined with any one or more of the other members to make additional sub-groups. For example, if the members of a group are a, b, c, d, and e, additional sub-groups specifically contemplated include any two, three, or four of the members, e.g., a and c; a, d, and e; b, c, d, and e; etc.

In some cases, the members of a first group of parameters, e.g., a, b, c, d, and e, may be combined with the members of a second group of parameters, e.g., A, B, C, D, and E. Any member of the first group or of a sub-group thereof may be combined with any member of the second group or of a sub-group thereof to form additional groups, i.e., b with C; a and c with B, D, and E, etc.

For example, in the present invention, groups of various parameters are defined (e.g. X, Y, n, $R^1$, $R^2$, $R^3$, $R^4$, $R^5$, and $R^6$). Each group contains multiple members. For example, $R^1$ represents alkyl, cycloalkyl, or aryl. Each member may be combined with each other member to form additional sub-groups, e.g., alkyl and cycloalkyl; alkyl and aryl; or cycloalkyl and aryl.

The instant invention further contemplates embodiments in which each element listed under one group may be combined with each and every element listed under any other group. For example, X is identified above as representing S, NH, $NR^3$, or O, wherein $R^3$ is $C_{1-5}$ alkyl. Y is identified above as representing —$CONHR^1$ or —$NHCOR^1$. Each element of X (S, NH, $NR^3$, or O) can be combined with each and every element of Y (—$CONHR^1$ or —$NHCOR^1$). For example, in one embodiment, X may be O and Y may be —$CONHR^1$. Alternatively, X may be S and Y may be —$NHCOR^1$. Similarly, a third group is $R^2$, in which the elements are defined as a substituted or unsubstituted 5, 6, 7, or 8-membered carbocyclic or heterocyclic ring containing at least one double bond. Each of the above embodiments may be combined with each and every element of $R^2$. For example, in the embodiment wherein X is $NR^3$, $R^3$ is methyl, and Y is —$CONHR^1$; $R^2$ may be phenyl (or any other chemical moiety within the element of $R^2$).

With each group, it is specifically contemplated that any one of more members can be excluded. For example, if X is defined as S, NH, NR³, or O, it is also contemplated that X is defined as S, NH, or O.

The compounds of this invention are limited to those that are chemically feasible and stable. Therefore, a combination of substituents or variables in the compounds described above is permissible only if such a combination results in a stable or chemically feasible compound. A stable compound or chemically feasible compound is one in which the chemical structure is not substantially altered when kept at a temperature of 40° C. or less, in the absence of moisture or other chemically reactive conditions, for at least a week.

All stereoisomers of the compounds of the instant invention are contemplated, either in admixture or in pure or substantially pure form. The definition of compounds according to the invention embraces all the possible stereoisomers and their mixtures; it also embraces the racemic forms and the isolated optical isomers having the specified activity. The racemic forms can be resolved by physical methods, such as, for example, fractional crystallization, separation, or crystallization of diastereomeric derivatives or separation by chiral column chromatography. The individual optical isomers can be obtained from the racemates from the conventional methods, such as, for example, salt formation with an optically active acid followed by crystallization.

A list following the word "comprising" is inclusive or open-ended, i.e., the list may or may not include additional unrecited elements. A list following the words "consisting of" is exclusive or closed ended, i.e., the list excludes any element not specified in the list.

All numbers in the specification are approximate unless indicated otherwise.

Synthesis of Compounds

The compounds of the invention may be synthesized by methods known in the art. Reaction Scheme 1 represents one approach to the synthesis of some compounds of Formulas I and II. Other compounds of the invention may be synthesized similarly using synthetic techniques known in art.

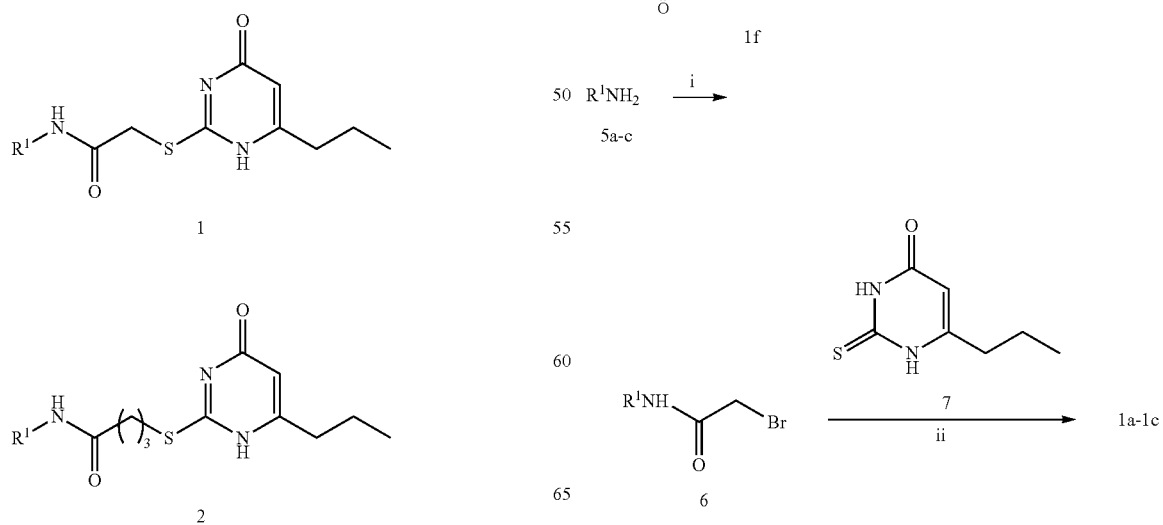

-continued

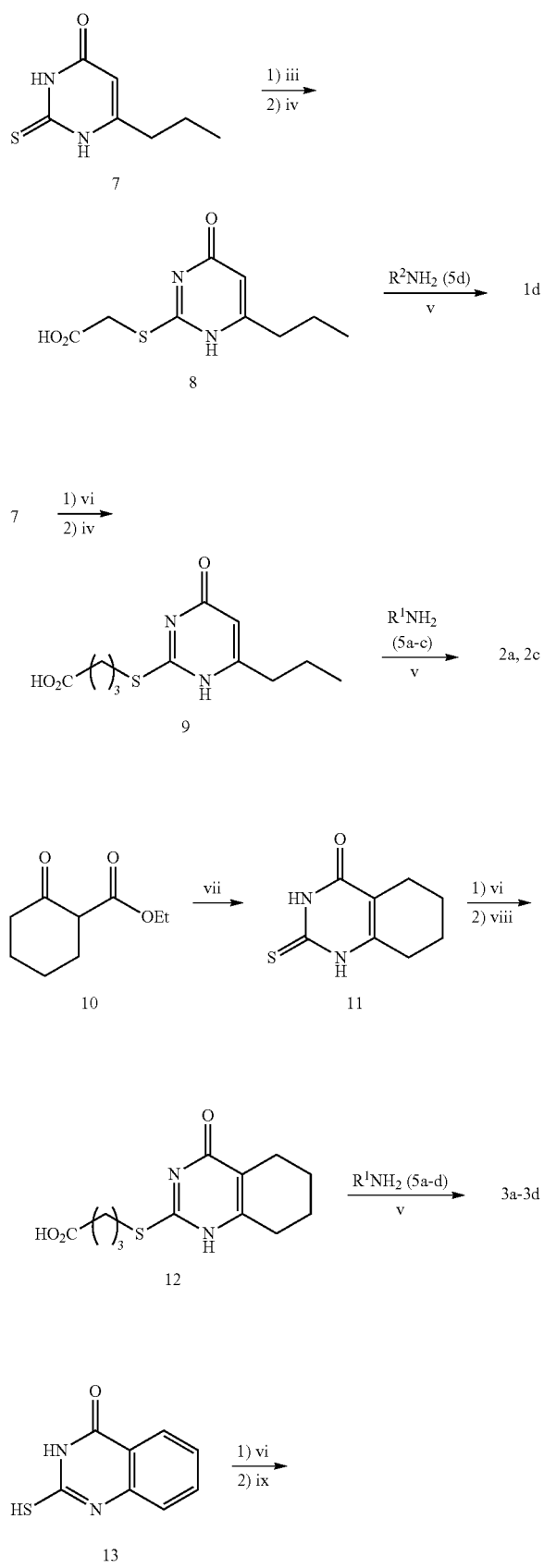

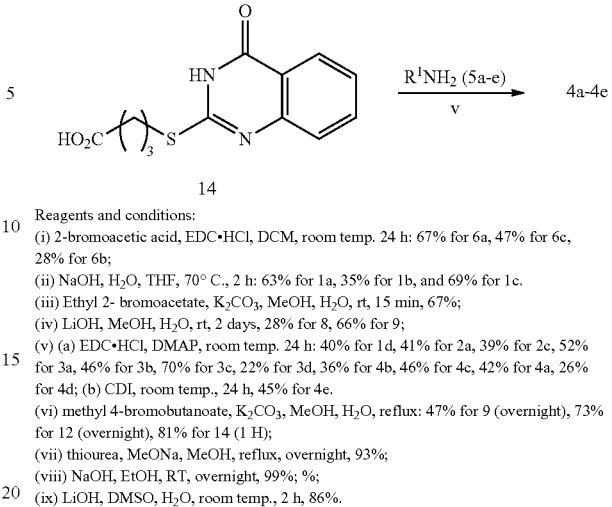

Reagents and conditions:
(i) 2-bromoacetic acid, EDC•HCl, DCM, room temp. 24 h: 67% for 6a, 47% for 6c, 28% for 6b;
(ii) NaOH, H₂O, THF, 70° C., 2 h: 63% for 1a, 35% for 1b, and 69% for 1c.
(iii) Ethyl 2- bromoacetate, K₂CO₃, MeOH, H₂O, rt, 15 min, 67%;
(iv) LiOH, MeOH, H₂O, rt, 2 days, 28% for 8, 66% for 9;
(v) (a) EDC•HCl, DMAP, room temp. 24 h: 40% for 1d, 41% for 2a, 39% for 2c, 52% for 3a, 46% for 3b, 70% for 3c, 22% for 3d, 36% for 4b, 46% for 4c, 42% for 4a, 26% for 4d; (b) CDI, room temp., 24 h, 45% for 4e.
(vi) methyl 4-bromobutanoate, K₂CO₃, MeOH, H₂O, reflux: 47% for 9 (overnight), 73% for 12 (overnight), 81% for 14 (1 H);
(vii) thiourea, MeONa, MeOH, reflux, overnight, 93%;
(viii) NaOH, EtOH, RT, overnight, 99%; %;
(ix) LiOH, DMSO, H₂O, room temp., 2 h, 86%.

Compound 1a in Reaction Scheme 1 was synthesized using the synthetic route shown in Reaction Scheme 1. The synthesis commenced with the reaction of aniline 5a with bromoacetic acid in the presence of EDC·HCl to afford bromoacetanilide 6a as white solid in 67% yield. Subsequently, 6a was reacted with thiouracil 7 in aqueous NaOH and heated to 70° C. for 48 hours to give compound 1a in 63% yield as a white solid after recrystallization. In addition, compounds 1b and 1c were synthesized using the same synthetic process.

Closely related compound 1d bearing a benzimidazole group was synthesized using a different route. In this synthesis, thiouracil 7 was converted to the corresponding thioacetic acid 8, followed by the amide coupling with 2-aminobenzimidazole to give compound 1d in modest yield.

Synthesis of compounds 2a and 2c followed the same strategy as that for compound 1d by converting 7 to the corresponding thiobutanoic acid 9, followed by amide formation by coupling In a similar manner, compounds 3a-d were synthesized in moderate yields through the coupling of anilines and 2-aminobenzimidazole with thiobutanoic acid 12, prepared from 2-sulfhydryl-5,6,7,8-tetrahydroquinazolin-4(3H)-one (11) as shown. Compound 11 was readily prepared by reacting keto ester 10 with thiourea and a base. Compounds 4a-e were synthesized in moderate yields using the same strategy except for starting from 2-sulfhydryltetrahydroquinazolinone (13) and employed anilines and 2-aminoimidazole for the amide formation.

Uses of Compounds of the Invention

In another embodiment, the invention relates to a method of treating cancer in a patient in need thereof, including administering a therapeutically effective amount of one or more compound of the invention, i.e., a compound according to Formula I or II, or a pharmaceutically acceptable salt thereof.

The compounds used in the method of the present invention may be in a salt form. As used herein, a "salt" is a salt of the instant compounds which has been modified by making acid or base salts of the compounds. Examples of pharmaceutically acceptable salts include, but are not limited to, mineral or organic acid salts of basic residues such as amines; alkali or organic salts of acidic residues such as phenols. The salts can be made using an organic or inorganic acid. Such acid salts are chlorides, bromides, sulfates, nitrates, phosphates, sulfonates, formates, tartrates, maleates, malates, citrates, benzoates, salicylates, ascorbates, and the like. Phenolate salts are the alkaline earth metal salts, sodium, potassium or lithium. The term "pharmaceutically acceptable salt" in this respect, refers to the relatively non-toxic, inorganic and organic acid or base addition salts of compounds of the present invention. These salts can be prepared in situ during the final isolation and purification of the compounds of the invention, or by separately reacting a purified compound of the invention in its free base or free acid form with a suitable organic or inorganic acid or base, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", J. Pharm. Sci. 66:1-19).

The compounds of the present invention may also form salts with basic amino acids such a lysine, arginine, etc. and with basic sugars such as N-methylglucamine, 2-amino-2-deoxyglucose, etc. and any other physiologically non-toxic basic substance.

The compounds used in the method of the present invention may be administered in various forms, including those detailed herein. The treatment with the compound may be a component of a combination therapy or an adjunct therapy, i.e. the subject or patient in need of the drug is treated or given another drug for the disease in conjunction with one or more of the instant compounds. This combination therapy can be sequential therapy where the patient is treated first with one drug and then the other or the two drugs are given simultaneously. These can be administered independently by the same route or by two or more different routes of administration depending on the dosage forms employed.

As used herein, a "pharmaceutically acceptable carrier" is a pharmaceutically acceptable solvent, suspending agent or vehicle, for delivering the instant compounds to the animal or human. The carrier may be liquid or solid and is selected with the planned manner of administration in mind. Liposomes are also a pharmaceutically acceptable carrier as are slow-release vehicles.

A therapeutically effective amount of the compounds of the invention or a pharmaceutically acceptable salt thereof is any amount effective to treat a cancer patient. Modes of administration and doses can be determined by a person having skill in the art. For example, the dosage of the compounds administered in treatment will vary depending upon factors such as the pharmacodynamic characteristics of a specific chemotherapeutic agent and its mode and route of administration; the age, sex, metabolic rate, absorptive efficiency, health and weight of the recipient; the nature and extent of the symptoms; the kind of concurrent treatment being administered; the frequency of treatment with; and the desired therapeutic effect.

A dosage unit of the compounds used in the method of the present invention may comprise a single compound or mixtures thereof with additional antitumor agents. The compounds can be administered in oral dosage forms as tablets, capsules, pills, powders, granules, elixirs, tinctures, suspensions, syrups, and emulsions. The compounds may also be administered in intravenous (bolus or infusion), intraperitoneal, subcutaneous, or intramuscular form, or introduced directly, e.g. by injection, topical application, or other methods, into or topically onto a site of disease or lesion, all using dosage forms well known to those of ordinary skill in the pharmaceutical arts.

The compounds used in the method of the present invention can be administered in admixture with suitable pharmaceutical diluents, extenders, excipients, or in carriers such as the novel programmable sustained-release multi-compartmental nanospheres (collectively referred to herein as a pharmaceutically acceptable carrier) suitably selected with respect to the intended form of administration and as consistent with conventional pharmaceutical practices. The unit will be in a form suitable for oral, nasal, rectal, topical, intravenous or direct injection or parenteral administration. The compounds can be administered alone or mixed with a pharmaceutically acceptable carrier. This carrier can be a solid or liquid, and the type of carrier is generally chosen based on the type of administration being used. The active agent can be co-administered in the form of a tablet or capsule, liposome, as an agglomerated powder or in a liquid form. Examples of suitable solid carriers include lactose, sucrose, gelatin and agar. Capsule or tablets can be easily formulated and can be made easy to swallow or chew; other solid forms include granules, and bulk powders. Tablets may contain suitable binders, lubricants, diluents, disintegrating agents, coloring agents, flavoring agents, flow-inducing agents, and melting agents. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents. Oral dosage forms optionally contain flavorants and coloring agents. Parenteral and intravenous forms may also include minerals and other materials to make them compatible with the type of injection or delivery system chosen.

Techniques and compositions for making dosage forms useful in the present invention are described in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol. 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modern Pharmaceutics Drugs and the Pharmaceutical Sciences, Vol 40 (Gilbert S. Banker, Christopher T. Rhodes, Eds.).

Examples have been set forth below for the purposes of illustration and to describe the best mode of the invention at the present time. The scope of the invention is not to be in any way limited by the examples set forth herein.

EXAMPLES

Example 1. Synthesis and Characterization of Compounds 1a to 4e

N-(4-Difluoromethoxyphenyl)-2-(4-oxo-6-propyl-1,4-dihydropyrimidin-2-ylthio)acetamide (1a)

To a solution of bromoacetic acid (170 mg, 1.25 mmol) and EDC·HCl (239 mg, 1.25 mmol) in dichloromethane (6 mL) was added aniline (5a, 200 mg, 1.25 mmol) and stirred at room temperature overnight. After the completion of the reaction, the reaction mixture was diluted with dichloromethane and washed twice with 1 N hydrochloric acid, twice with saturated solution of sodium bicarbonate and twice with brine. The organic layers were collected, dried over magnesium sulfate, filtered and concentrated to afford an off-white crude product. The crude product was recrystallized from hexanes/dichloromethane to give bromoacetanilide 6a as white solid (227 mg, 65% yield): $^1$H NMR (300 MHz, CDCl3) δ 4.27 (s, 2H), 6.30-6.79 (s, 1H), 7.21 (d, 2H, J=9 Hz), 7.63 (d, 2H, J=9 Hz).

To a solution of sodium hydroxide (7.2 mg, 0.18 mmol) in water (2 mL) was added 2-hydrosulfanyl-4-oxo-6-propyl-1,4-dihydropyrimidine (7) (30 mg, 0.18 mmol) and the mixture was stirred till all of 1 were dissolved. To the mixture was added a solution of 6a (50 mg, 0.18 mmol) in tetrahydrofuran (2 mL) and heated at 60° C. for 2 h and then at 70° C. overnight. After the completion of reaction white precipitate was observed which was collected on a filter and recrystallized from ethanol to afford 1a as white solid (42 mg, 63% yield): mp. 180° C. (decomp.); $^1$H NMR (700 MHz, DMSO-$d_6$) δ 0.73 (t, J=7.0 Hz, 3H), 1.51 (m, 2H), 2.32 (t, J=7.0 Hz, 2H), 4.05 (s, 2H), 5.97 (s, 1H), 6.97-7.29 (m, 3H), 7.62 (d, J=8.4 Hz, 2H), 10.44 (s, 1H); $^{13}$C NMR (175 MHz, DMSO-$d_6$) δ 13.4, 20.6, 35.1, 38.2, 116.5.0 (t, J=256.0 Hz), 119.5, 120.4, 136.4, 146.3, 165.9; $^{19}$F NMR (376 MHz, DMSO-$d_6$) δ −81.6; HRMS (ESI+) calcd for $C_{16}H_{18}F_2N_3O_3S$ [M+H]$^+$ 370.1031, found 370.1039 (Δ=−2.02 ppm).

In the same manner, 1b and 1c were synthesized.

2-(4-Oxo-6-propyl-1,4-dihydropyrimidin-2-ylthio)-N-phenylacetamide (1b)

White solid; 35% yield; mp. 170° C. (decomposed); $^1$H NMR (700 MHz, DMSO-$d_6$) δ $^1$H NMR (700 MHz, DMSO-$d_6$) δ 0.83 (t, J=7.0 Hz, 3H), 1.46-1.56 (m, 2H), 2.31 (t, J=7.0 Hz, 2H), 4.04 (s, 2H), 5.90 (s, 1H), 7.04 (t, J=7.7 Hz, 1H), 7.30 (t, J=7.7 Hz, 2H), 7.56 (t, J=7.7 Hz, 2H), 10.33 (s, 1H), 12.67 (s, 1H). $^{13}$C NMR (175 MHz, DMSO-$d_6$) δ 13.4, 20.5, 35.1, 38.5, 119.0, 123.3, 128.7, 139.0, 165.9; HRMS (ESI+) calcd for $C_{15}H_{18}N_3O_2S$ [M+H]$^+$ 304.1114, found 304.1113 (Δ=0.29 ppm).

N-(4-Fluorophenyl)-2-(4-oxo-6-propyl-1,4-dihydropyrimidin-2-ylthio)acetamide (1c)

White solid; 69% yield; mp. 191-194° C.; $^1$H NMR (500 MHz, DMSO-$d_6$) δ 0.73 (t, J=7.0 Hz, 3H), 1.45-1.56 (m, 2H), 2.31 (t, J=7.0 Hz, 2H), 4.02 (s, 2H), 6.94 (s, 1H), 7.10-7.19 (m, 2H), 7.55-7.62 (m, 2H), 10.30 (s, 1H), 12.54 (s, 1H). $^{13}$C NMR (500 MHz, DMSO-$d_6$) δ 13.4, 20.5, 35.0, 38.5, 115.3 (d, J=22.1 Hz), 120.7 (d, J=7.7 Hz), 135.5 (d, J=2.5 Hz), 158.0 (d, J=238.4 Hz), 165.8; $^{19}$F NMR (376 MHz, DMSO-$d_6$) δ −119.3; HRMS (ESI+) calcd for $C_{15}H_{17}FN_3O_2S$ [M+H]$^+$ 322.1020, found 322.1020 (Δ=−0.03 ppm).

N-(1H-benzo[d]imidazol-2-yl)-2-(4-oxo-6-propyl-1,4-dihydropyrimidin-2-ylthio)acetamide (1d)

To a solution of thiouracil 7 (1.70 g, 10.0 mmol) and potassium carbonate (2.07 g, 15.0 mmol) in MeOH (10 mL) and water (20 mL) was added ethyl 2-bromoacetate (1.42 g, 8.5 mmol). The mixture was stirred at room temperature for 15 min and 50 mL water was added. Then, the reaction mixture was extracted with ethyl acetate (5×80 mL). The organic layers were combined and washed with water (100 mL) and brine (100 mL), dried over MgSO$_4$, and the solvent was removed by rotary evaporator. The crude product was purified by flash column chromatography on silica gel using MeOH/DCM as eluent to give ethyl 2-(4-oxo-6-propyl-1,4-dihydropyrimidin-2-ylthio)acetate as white solid (1.7 g, 67% yield): mp. 117-118° C.; $^1$H NMR (300 MHz, CDCl$_3$) δ 0.93 (t, J=7.2 Hz, 3H), 1.27 (t, J=7.2 Hz, 3H), 1.59-1.65 (m, 2H), 2.43 (t, J=7.2 Hz, 2H), 3.93 (s, 2H), 4.20 (q, J=7.2 Hz, 2H), 6.05 (s, 1H), 13.17 (s, 1H). $^{13}$C NMR (175 MHz, CDCl$_3$) δ 13.6, 14.1, 20.8, 32.8, 39.5, 61.9, 108.2, 158.9, 165.5, 168.2, 169.2; HRMS (ESI+) calcd for $C_{11}H_{17}N_2O_3S$ [M+H]$^+$ 257.0954, found 257.0953 (Δ=0.48 ppm).

To a solution of ethyl 2-((4-oxo-6-propyl-1,4-dihydropyrimidin-2-yl)thio)acetate (1.20 g, 4.68 mmol) in MeOH and water was added lithium hydroxide (0.2 g, 9.36 mmol). The mixture was stirred at room temperature for 2 days. The reaction mixture was adjusted to pH 1 by 1N hydrochloric acid, and extracted with ethyl acetate (5×80 mL). The organic layers were combined and dried over MgSO$_4$, and the solvent was removed by rotary evaporator to afford thioacetic acid 8 (0.30 g, 28%) as white solid: mp. 154-155° C.; $^1$H NMR (700 MHz, DMSO-$d_6$) δ 0.86 (t, J=7.0 Hz, 3H), 1.56 (m, 2H), 2.30 (t, J=7.0 Hz, 2H), 3.47 (s, 2H), 5.79 (s, 1H). $^{13}$C NMR (175 MHz, DMSO-$d_6$) δ 13.6, 20.7, 36.1, 38.2, 107.4, 163.7, 164.3, 166.3, 171.2; HRMS (ESI+) calcd for $C_9H_{13}N_2O_3S$ [M+H]$^+$ 229.0641, found 229.0644 (Δ=−1.11 ppm).

To a mixture of 2-(6-oxo-4-propyl-1,6-dihydropyrimidin-2-ylthio)acetic acid (8) (228 mg, 1.0 mmol), 1H-benzo[d]imidazol-2-amine (5d, 146 mg, 1.1 mmol) and DMAP (134 mg, 1.1 mmol) in DMF (3 mL) was added EDC·HCl (211 mg, 1.1 mmol), and the mixture was stirred at RT for 24 h. 50 mL water was added, and the resulting precipitate was filtered to give a solid, which was recrystallized from 1,4-dioxane to give compound 1d (136 mg, 40%) as off-white solid: mp. 217° C. (decomposed); $^1$H NMR (700 MHz, DMSO-$d_6$) δ 0.63 (t, J=7.0 Hz, 3H), 1.50-1.40 (m, 2H), 2.27 (t, J=7.0 Hz, 2H), 4.14 (s, 2H), 5.93 (s, 1H), 7.05-7.09 (m, 2H), 7.40-7.43 (m, 2H), 12.10 (s, 3H); $^{13}$C NMR (175 MHz, DMSO-$d_6$) δ 13.3, 20.5, 34.5, 38.4, 106.5, 111.5, 114.1, 120.3, 121.0, 136.3, 146.7, 161.6, 162.3, 163.9, 167.7; HRMS (ESI+) calcd for $C_{16}H_{18}N_5O_2S$ [M+H]$^+$ 344.1176, found 344.118 (Δ=−1.1 ppm).

N-(4-Difluoromethoxyphenyl)-4-(4-oxo-6-propyl-1,4-dihydropyrimidin-2-ylthio)butanamide (2a)

To a solution of thiouracil 7 (0.85 g, 5 mmol) and potassium carbonate (1.03 g, 7.5 mmol) in methanol (5 mL) and water (10 mL) was added methyl 4-bromobutanoate (1.36 g, 7.5 mmol). The solution was heated to reflux overnight. The reaction mixture was cooled to room temperature, 50 mL water was added, and the mixture was extracted with ethyl acetate (3×50 mL). The organic layers were combined and washed with water (50 mL) and brine (50 mL), dried over MgSO$_4$, the solvent was removed by rotary evaporator. The crude product was purified by flash column chromatography on silica gel using MeOH/DCM as eluent to give methyl 4-(4-oxo-6-propyl-1,4-dihydropyrimidin-2-ylthio)butanoate as white solid (0.64 g, 47% yield): mp. 129-130° C.; $^1$H NMR (500 MHz, CDCl$_3$) δ 0.95 (t, J=7.0 Hz, 3H), 1.64-1.71 (m, 2H), 2.06 (m, 2H), 2.46 (m, 4H), 3.24 (t, J=7.0 Hz, 2H), 3.68 (s, 3H), 6.04 (s, 1H), 12.99 (s, 1H); $^{13}$C NMR (125 MHz, CDCl$_3$) δ 13.8, 21.0, 24.7, 29.9, 32.7, 39.7, 51.8, 108.0, 160.2, 165.6, 169.5, 173.4; HRMS (ESI+) calcd for C$_{12}$H$_{19}$N$_2$O$_3$S [M+H]$^+$ 271.1111, found 271.111 (Δ=0.51 ppm).

To a solution of methyl 4-(4-oxo-6-propyl-1,4-dihydropyrimidin-2-ylthio)butanoate (500 mg, 1.84 mmol) in MeOH and water was added lithium hydroxide (88.1 mg, 3.68 mmol), and the mixture was stirred at room temperature for 2 days. The mixture was adjusted to pH 1 by 1N hydrochloric acid to form white precipitate. The precipitate was collected on a filter to afford 4-(4-oxo-6-propyl-1,4-dihydropyrimidin-2-ylthio)butanoic acid 9 as white solid (308.0 mg, 66% yield): mp. 139-141° C.; $^1$H NMR (300 MHz, CDCl$_3$) δ 0.95 (t, J=7.3 Hz, 3H), 1.68 (m, 2H), 2.01-2.14 (m, 2H), 2.49 (m, 4H), 3.28 (t, J=6.5 Hz, 2H), 6.04 (s, 1H); $^{13}$C NMR (175 MHz, CDCl$_3$) δ 13.8, 21.1, 24.5, 29.9, 32.8, 39.7, 107.7, 160.3, 165.9, 170.2, 178.5; HRMS (ESI+) calcd for C$_{11}$H$_{17}$N$_2$O$_3$S [M+H]$^+$ 257.0954, found 257.0958 (Δ=-1.33 ppm).

To a mixture of 9 (190 mg, 0.74 mmol), 4-(difluoromethoxy)aniline (5a, 130.5 mg, 0.82 mmol) and 4-(dimethylamino)pyridine (DMAP) (99.4 mg, 0.81 mmol) in dimethylformamide (DMF) (3 mL) was added N'-ethylcarbodiimide hydrochloride (EDC-HCl (156 mg, 0.81 mmol), the mixture was stirred at room temperature for 1 h. Then, 100 mL water was added to the reaction mixture to form off-white precipitate, which was collected on a filter to give an off-white solid. The solid was dissolved in ethyl acetate and dried over MgSO$_4$, filtered, and the solvent was removed by rotary evaporator. The crude product was purified by recrystallization from ethyl acetate/hexane to afford 2a as white solid (120.4 mg, 41% yield): mp. 174-177° C.; $^1$H NMR (500 MHz, CDCl$_3$) δ 0.92 (t, J=7.5 Hz, 3H), 1.64 (m, 2H), 2.06-2.22 (m, 2H), 2.42 (t, J=7.5 Hz, 2H), 2.49 (t, J=6.9 Hz, 2H), 3.31 (t, J=5.7 Hz, 2H), 6.01 (s, 1H), 6.45 (t, J=74.0 Hz, 1H), 7.07 (d, J=8.6 Hz, 2H), 7.55 (d, J=8.6 Hz, 2H), 7.92 (s, 1H), 12.69 (s, 1H). $^{13}$C NMR (125 MHz, CDCl$_3$) δ 13.8, 21.1, 24.8, 30.2, 35.5, 39.7, 107.8, 116.1 (t, J=259 Hz), 120.6, 121.3, 135.6, 147.3, 160.2, 165.5, 169.9, 170.5; $^{19}$F NMR (376 MHz, CDCl$_3$) δ -80.7; HRMS (ESI+) calcd for C$_{18}$H$_{22}$F$_2$N$_3$O$_3$S [M+H]$^+$ 398.1344, found 398.1345 (Δ=-0.03 ppm). In the same manner, compound 2c was synthesized.

N-(4-Fluorophenyl)-4-(4-oxo-6-propyl-1,4-dihydropyrimidin-2-ylthio)butanamide (2c)

White solid; 39% yield. mp. 180-182° C.; $^1$H NMR (300 MHz, CDCl$_3$) δ 0.83-0.96 (t, J=7.3 Hz, 3H), 1.57-1.69 (m, 2H), 2.05-2.21 (m, 2H), 2.33-2.55 (m, 4H), 3.31 (t, J=6.3 Hz, 2H), 6.02 (s, 1H), 7.00 (t, J=8.7 Hz, 2H), 7.49 (m, 2H), 7.64 (s, 1H), 12.45 (s, 1H). $^{13}$C NMR (175 MHz, DMSO-d$_6$) δ 13.4, 20.5, 24.8, 29.2, 34.9, 38.5, 115.2 (d, J=22.0 Hz), 120.7 (d, J=7.7 Hz), 135.7 (d, J=2.3 Hz), 157.1, 158.5, 170.3; $^{19}$F NMR (376 MHz, CDCl$_3$) δ -119.7; HRMS (ESI+) calcd for C$_{17}$H$_{21}$FN$_3$O$_2$S [M+H]$^+$ 350.1333, found 350.134 (Δ=-2.12 ppm).

4-(4-Oxo-3,4,5,6,7,8-hexahydroquinazolin-2-ylthio)-N-phenylbutanamide (3b)

Ethyl 2-oxocyclohexane-1-carboxylate 10 (1.70 g, 10.0 mmol) and thiourea (1.52 g, 20.0 mmol) were added to a sodium methoxide solution (0.58 g sodium in 20 mL methanol), and the mixture was refluxed overnight. The solvent was removed and the residue was dissolved in hot water (50 mL). Glacial acetic acid (6 mL) was added dropwise to make the solution acidic until a white solid was formed. The precipitate was collected by a filter and washed successively with saturated sodium bicarbonate (3×10 mL) and water (3×10 mL), and recrystallized from ethyl acetate (30 mL) to afford 2-sulfhydryl-5,6,7,8-tetrahydroquinazolin-4(3H)-one (11) (1.70 g, 93%) as white solid: mp.>230° C.; 1H NMR (700 MHz, DMSO-d6) δ 1.53-1.76 (m, 4H), 2.16 (t, J=6.0 Hz, 2H), 2.36 (t, J=6.0 Hz, 2H), 12.09 (s, 1H), 12.25 (s, 1H); 13C NMR (175 MHz, DMSO-d6) δ 20.5, 20.7, 20.9, 25.5, 111.6, 149.5, 161.3, 173.9; HRMS (ESI+) calcd for C8H11N2OS [M+H]$^+$ 183.0587, found 183.0587 (Δ=-0.44 ppm).

To a solution of 11 (1.59 g, 8.72 mmol) in anhydrous methanol (15 mL) was added methyl 4-bromobutanoate (1.72 g, 9.55 mmol) and potassium carbonate (1.31 g, 9.48 mmol). The reaction mixture was heated to reflux for overnight. After cooled to room temperature, the reaction mixture was concentrated in vacuo to remove the solvent. To the residue water (50 mL) was added, and extracted with dichloromethane (4×40 mL). The combined organic phases were washed with brine (5 mL), dried over MgSO$_4$, and concentrated in vacuo to give a crude product, which was purified by recrystallization from ethyl acetate to afford methyl 4-(4-oxo-3,4,5,6,7,8-hexahydroquinazolin-2-ylthio)butanoate (1.80 g, 73%) as white solid: mp. 149-150° C.; $^1$H NMR (700 MHz, CDCl$_3$) δ 1.69-1.79 (m, 4H), 2.01-2.06 (m, 2H), 2.47 (m, 4H), 2.59 (t, J=7.0 Hz, 2H), 3.22 (t, J=7.0 Hz, 2H), 3.67 (s, 3H); $^{13}$C NMR (175 MHz, CDCl$_3$) δ 21.7, 21.8, 22.2, 24.7, 29.8, 31.6, 32.7, 51.8, 117.6, 156.4, 162.0, 165.0, 173.5; HRMS (ESI+) calcd for C$_{13}$H$_{19}$N$_2$O$_3$S [M+H]$^+$ 283.1111, found 283.1117 (Δ=-2.09 ppm).

To a mixture of 2 N sodium hydroxide (1.51 g in 19 mL water) and ethanol (22 mL) was added methyl 4-(4-oxo-3,4,5,6,7,8-hexahydroquinazolin-2-ylthio)butanoate (1.34 g, 4.75 mmol) at room temperature. The mixture was stirred for overnight at room temperature. The reaction mixture was adjusted to pH 5 with 1N hydrochloric acid and extracted with dichloromethane (5×40 mL). The combined organic phases were dried over MgSO$_4$, and concentrated in vacuo to give a residue, which was recrystallized from dichloromethane to afford 4-(4-oxo-3,4,5,6,7,8-hexahydroquinazolin-2-ylthio)butanoic acid 12 (1.26 g, 99% yield) as white solid: mp. 176-177° C.; $^1$H NMR (700 MHz, CD$_3$OD) δ 1.71-1.81 (m, 4H), 1.96-2.03 (m, 2H), 2.39 (t, J=6.3 Hz, 2H), 2.43 (t, J=7.0 Hz, 2H), 2.57 (t, J=6.3 Hz, 2H), 3.23 (t, J=7.0 Hz, 2H); $^{13}$C NMR (175 MHz, CD$_3$OD) δ 22.7, 22.9, 23.1, 26.0, 30.4, 33.4, 176.6; HRMS (ESI+) calcd for C$_{12}$H$_{17}$N$_2$O$_3$S [M+H]$^+$ 269.0954, found 269.0959 (Δ=-1.54 ppm).

To a mixture of thiobutanoic acid 12 (134 mg, 0.50 mmol), aniline 5b (70 mg, 0.75 mmol) and DMAP (67 mg, 0.55 mmol) in DMF (2 mL) was added EDC-HCl (105 mg, 0.55 mmol), and the mixture was stirred at room temperature for 48 h. To the reaction mixture 50 mL water was added with stirring to form precipitate. The resulting precipitate was collected on a filter and recrystallized from ethyl acetate to give 3b (79 mg, 46% yield) as an off-white solid: mp. 193-194° C.; $^1$H NMR (500 MHz, DMSO-$d_6$) δ 1.56-1.67 (m, 4H), 1.91-1.97 (m, 2H), 2.26 (m, 2H), 2.39-2.45 (m, 4H), 3.16 (t, J=7.0 Hz, 2H), 7.01 (t, J=8.0 Hz, 1H), 7.27 (t, J=8.0 Hz, 2H), 7.58 (d, J=8.0 Hz, 2H), 9.90 (s, 1H), 12.42 (s, 1H); $^{13}$C NMR (125 MHz, DMSO-$d_6$) δ 21.4, 21.8, 24.7, 29.0, 31.1, 34.9, 119.0, 122.9, 128.6, 139.3, 170.3; HRMS (ESI+) Calcd for $C_{18}H_{22}N_3O_2S$ [M+H]$^+$ 344.1427, found 344.1430 (Δ=−0.71 ppm).

In the same manner, compounds 3a, 3c, and 3d were synthesized.

N-(4-Difluoromethoxyphenyl)-4-(4-oxo-3,4,5,6,7,8-hexahydroquinazolin-2-ylthio)butanamide (3a)

Off-white solid; 52% yield; mp. 197-198° C.; $^1$H NMR (700 MHz, Acetone-$d_6$) δ 1.63-1.73 (m, 4H), 2.09 (m, 2H), 2.35 (t, J=6.3 Hz, 2H), 2.47 (t, J=6.3 Hz, 2H), 2.53 (t, J=7.0 Hz, 2H), 3.27 (t, J=7.0 Hz, 2H), 6.90 (t, J=74.4 Hz, 1H), 7.11 (d, J=8.4 Hz, 2H), 7.70 (d, J=8.4 Hz, 2H), 9.27 (s, 1H), 11.46 (s, 1H); $^{13}$C NMR (175 MHz, Acetone-$d_6$) δ 22.4, 22.5, 23.0, 26.0, 32.2, 35.9, 117.6 (t, J=255.5 Hz), 117.9, 120.6, 121.3, 137.9, 147.6 (t, J=2.6 Hz), 157.2, 161.2, 163.4, 171.2; $^{19}$F NMR (376 MHz, Acetone-$d_6$) δ −82.3; HRMS (ESI+) Calcd for $C_{19}H_{22}F_2N_3O_3S$[M+H]$^+$ 410.1344, found 410.1346 (Δ=−0.33 ppm).

N-(4-Fluorophenyl)-4-(4-oxo-3,4,5,6,7,8-hexahydroquinazolin-2-ylthio)butanamide (3c)

White solid; 70% yield; mp. 211.5-213° C.; $^1$H NMR (700 MHz, DMSO-$d_6$) δ 1.56-1.66 (m, 4H), 1.94 (m, 2H), 2.26 (t, J=5.6 Hz, 2H), 2.41 (t, J=7.0 Hz, 4H), 3.15 (t, J=7.0 Hz, 2H), 7.10-7.14 (m, 2H), 7.57-7.61 (m, 2H), 9.96 (s, 1H), 12.44 (s, 1H); $^{13}$C NMR (175 MHz, DMSO-$d_6$) δ 21.4, 21.8, 24.7, 29.0, 31.1, 34.8, 115.2 (d, J=21.9 Hz), 120.7 (d, J=7.7 Hz), 135.7 (d, J=2.3 Hz), 157.8 (d, J=238 Hz), 170.3; $^{19}$F NMR (376 MHz, DMSO-$d_6$) δ −119.8; HRMS (ESI+) calcd for $C_{18}H_{21}FN_3O_2S$ [M+H]$^+$ 362.1333, found 362.1337 (Δ=−1.05 ppm).

N-(1H-Benzo[d]imidazol-2-yl)-4-(4-oxo-3,4,5,6,7,8-hexahydroquinazolin-2-ylthio)butanamide (3d)

Off-white solid; 22% yield; mp.>230° C.; $^1$H NMR (700 MHz, DMSO-$d_6$) δ 1.55-1.66 (m, 4H), 2.09 (m, 2H), 2.21-2.27 (m, 2H), 2.35-2.41 (m, 2H), 3.21 (t, J=5.6 Hz, 2H), 3.27 (t, J=5.6 Hz, 2H), 6.93 (t, J=7.0 Hz, 1H), 7.11-7.22 (m, 2H), 7.38-7.48 (m, 3H), 12.45 (s, 1H); $^{13}$C NMR (125 MHz, DMSO-$d_6$)) δ 21.4, 21.8, 23.7, 28.5, 31.0, 36.2, 113.6, 115.7, 116.4, 119.5, 124.1, 130.0, 143.4, 154.6, 156.5, 160.0, 162.4, 173.8; HRMS (ESI+) Calcd for $C_{19}H_{22}N_5O_2S$[M+H]$^+$ 384.1489, found 384.1494 (Δ=−1.45 ppm).

4-(4-Oxo-3,4-dihydroquinazolin-2-ylthio)-N-phenylbutanamide (4b)

A mixture of 2-sulfhydrylquinazolin-4(3H)-one (13) (1.78 g, 10.0 mmol), methyl 4-bromobutanoate (2.72 g, 15.0 mmol) and $K_2CO_3$ (2.07 g, 15.0 mmol) in methanol (10 mL) and water (20 mL) was refluxed for 1 h. After cooled to room temperature, 50 mL water was added and the reaction mixture was extracted with ethyl acetate (3×50 mL). The combined organic layers were washed with (50 mL) and brine (50 mL), dried over $MgSO_4$, and concentrated in vacuo to give a crude product, which was purified by recrystallization from ethyl acetate/hexanes to give methyl 4-(4-oxo-3,4-dihydroquinazolin-2-ylthio)butanoate (2.24 g, 81% yield) as white solid: mp. 153-154° C.; $^1$H NMR (700 MHz, DMSO-$d_6$) δ 1.96 (m, 2H), 2.45 (t, J=7.0 Hz, 2H), 3.23 (t, J=7.0 Hz, 2H), 3.58 (s, 3H), 7.39 (t, J=7.0 Hz, 1H), 7.49 (d, J=7.0 Hz, 1H), 7.73 (t, J=7.0 Hz, 1H), 8.02 (d, J=7.0 Hz, 1H), 12.55 (s, 1H). $^{13}$C NMR (175 MHz, DMSO-$d_6$) δ 24.3, 28.9, 32.1, 51.4, 120.0, 125.6, 125.9, 126.0, 134.5, 148.3, 155.5, 161.3, 172.8. HRMS (ESI+) Calcd for $C_{13}H_{15}N_2O_3S$ [M+H]$^+$279.0798, found 279.0802 (Δ=−1.42 ppm).

A mixture of methyl 4-(4-oxo-3,4-dihydroquinazolin-2-ylthio)butanoate (1.39 g, 5.0 mmol) in DMSO (1 mL) and LiOH (aqueous, 1M, 10 mL) was stirred at room temperature for 2 h. To the reaction mixture was added 100 mL water and adjusted to pH 1. The resulting precipitate was collected on a filter, and washed with water to give 4-(4-oxo-3,4-dihydroquinazolin-2-ylthio)butanoic acid (14) (1.14 g, 86% yield) as white solid: mp. 178-179° C.; $^1$H NMR (500 MHz, DMSO-$d_6$) δ 1.90-1.96 (m, 2H), 2.37 (t, J=7.0 Hz, 2H), 3.24 (t, J=7.0 Hz, 2H), 7.41 (t, J=7.5 Hz, 1H), 7.52 (d, J=7.5 Hz, 1H), 7.75 (t, J=7.5 Hz, 1H), 8.02 (d, J=7.5 Hz, 1H), 12.37 (s, 2H). $^{13}$C NMR (175 MHz, DMSO-$d_6$) δ 24.3, 29.1, 32.5, 120.0, 125.6, 125.9, 126.0, 134.6, 148.3, 155.6, 161.3, 173.9; HRMS (ESI+) Calcd for $C_{12}H_{13}N_2O_3S$ [M+H]$^+$ 265.0641, found: 265.0646 (Δ=−1.56 ppm).

To a mixture of 4-(4-oxo-3,4-dihydroquinazolin-2-ylthio) butanoic acid (14) (132 mg, 0.50 mmol), aniline (186 mg, 2.0 mmol) and DMAP (67 mg, 0.55 mmol) in DMF (2 mL) was added EDC-HCl (144 mg, 0.75 mmol), and the mixture was stirred at room temperature for 18 h. To the reaction mixture was added 20 mL water with stirring. The resulting precipitate was collected on a filter and recrystallized from 1,4-dioxane to give 4b (61 mg, 36% yield) as white solid: mp.>230° C.; $^1$H NMR (700 MHz, DMSO-$d_6$) δ 1.56-1.60 (m, 2H), 2.03 (t, J=7.0 Hz, 2H), 2.84 (t, J=7.0 Hz, 2H), 6.57 (t, J=7.0 Hz, 1H), 6.83 (t, J=7.0 Hz, 2H), 6.95 (t, J=7.0 Hz, 1H), 7.01 (d, J=8.4 Hz, 1H), 7.13 (d, J=7.0 Hz, 2H), 7.25 (t, J=7.0 Hz, 1H), 7.57 (d, J=7.0 Hz, 1H), 9.48 (s, 1H), 12.12 (s, 1H); $^{13}$C NMR (175 MHz, DMSO-$d_6$) δ 24.8, 29.2, 35.1, 119.0, 112.0, 123.0, 125.6, 126.0, 128.6, 134.5, 139.3, 148.4, 155.6, 161.2, 170.4. HRMS (ESI+) Calcd for $C_{18}H_{18}N_3O_2S$ [M+H]$^+$340.1114, found: 340.1121 (Δ=−2.0 ppm).

In the same manner, compounds 4a, 4c, and 4d were synthesized.

N-(4-(Difluoromethoxy)phenyl)-4-(4-oxo-3,4-dihydroquinazolin-2-ylthio)butanamide (4a)

Off-white solid; 42% yield; mp. 210-211° C. $^1$H NMR (700 MHz, Acetone-$d_6$) δ 2.13-2.23 (m, 2H), 2.59 (t, J=7.0 Hz, 2H), 3.41 (t, J=7.0 Hz, 2H), 6.90 (t, J=74.2 Hz, 1H), 7.11 (d, J=8.4 Hz, 2H), 7.40 (t, J=7.7 Hz, 1H), 7.49 (d, J=7.7 Hz, 1H), 7.69 (m, 3H), 8.09 (d, J=7.7 Hz, 1H), 9.25 (s, 1H), 11.22 (s, 1H); $^{13}$C NMR (175 MHz, DMSO-$d_6$) δ 24.7, 29.2, 34.9, 116.5 (t, J=256 Hz), 119.5, 120.0, 120.4, 125.6, 126.0, 134.5, 136.7, 146.1, 148.40, 155.6, 161.3, 170.4; $^{19}$F NMR (376 MHz, DMSO-$d_6$) δ −81.4; HRMS (ESI+) Calcd for $C_{19}H_{18}F_2N_3O_3S$ [M+H]$^+$406.1031, found 406.1033 (Δ=−0.44 ppm).

N-(4-Fluorophenyl)-4-((4-oxo-3,4-dihydroquinazolin-2-yl)thio)butanamide (4c)

White solid; 46% yield; mp. 216-217° C.; $^1$H NMR (500 MHz, DMSO-$d_6$) δ 1.20-2.05 (m, 2H), 2.47 (t, J=7.0 Hz, 2H), 3.29 (t, J=7.0 Hz, 2H), 7.09-7.14 (m, 2H), 7.38-7.41 (m, 1H), 7.45 (d, J=8.0 Hz, 1H), 7.57-7.60 (m, 2H), 7.68-7.72 (m, 1H), 8.02 (dd, J=8.0, 1.5 Hz, 1H), 9.97 (s, 1H), 12.56 (s, 1H). $^{13}$C NMR (125 MHz, DMSO-$d_6$) δ 24.7, 29.2, 34.9, 115.2 (d, J=21.9 Hz), 112.0, 120.7 (d, J=7.7 Hz), 125.6, 126.0, 126.0, 134.5, 135.7 (d, J=2.4 Hz), 148.4, 155.5, 157.8 (d, J=237.9 Hz), 161.2, 170.3; $^{19}$F NMR (376 MHz, DMSO-$d_6$) δ −119.8; HRMS (ESI+) Calcd for $C_{18}H_{17}FN_3O_2S$ [M+H]$^+$358.1020, found: 358.1027 (Δ=−1.99 ppm).

N-(1H-Benzo[d]imidazol-2-yl)-4-(4-oxo-3,4-dihydroquinazolin-2-ylthio)butanamide (4d)

A white solid; 25% yield; mp.>230° C.; $^1$H NMR (700 MHz, DMSO-$d_6$) δ 2.05-2.09 (m, 2H), 2.61 (t, J=7.0 Hz, 2H), 3.31 (t, J=7.0 Hz, 2H), 7.07 (m, 2H), 7.33-7.50 (m, 4H), 7.58 (t, J=7.0 Hz, 1H), 8.00 (d, J=7.0 Hz, 1H), 11.52 (s, 1H), 12.06 (s, 1H), 12.57 (s, 1H); $^{13}$C NMR (175 MHz, DMSO-$d_6$) δ 24.5, 29.0, 31.1, 111.5, 116.9, 120.0, 121.8, 125.5, 126.0, 132.5, 134.4, 140.5, 146.6, 148.4, 155.6, 161.3, 171.8; HRMS (ESI+) Calcd for $C_{19}H_{17}N_5O_2S$ [M+H]$^+$ 380.1176, found 380.1178 (Δ=−0.54 ppm).

N-Hexyl-4-(4-oxo-3,4-dihydroquinazolin-2-ylthio)butanamide (4e)

To a mixture of 4-(4-oxo-3,4-dihydroquinazolin-2-ylthio) butanoic acid (14) (79 mg, 0.30 mmol) in 1,4-dioxane (2 mL) was added carbonyldiimidazole (CDI) (73 mg, 0.45 mmol), and the mixture was stirred at room temperature for 1 h. 1-Hexylamine (5e, 61 mg, 0.60 mmol) and DMF (5 mL) were added to the mixture and heated at 60° C. for 48 h. After cooled to room temperature, 40 mL water was added, and the reaction mixture was extracted with EtOAc (3×20 mL). The combined organic layers were washed with water (20 mL) and brine (20 mL), dried over MgSO$_4$, and concentrated in vacuo to give a yellow oil. Then, 20 mL hexane was added to this oil with stirring to form precipitate. The resulting precipitate was collected on a filter to give 4e (46.7 mg, 45% yield) as white solid: mp. 168-169° C. $^1$H NMR (700 MHz, DMSO-$d_6$) δ 0.81 (t, J=5.6 Hz, 3H), 1.20 (m, 6H), 1.35 (m, 2H), 1.92 (m, 2H), 2.22 (t, J=7.0 Hz, 2H), 3.01 (m, 2H), 3.20 (t, J=7.0 Hz, 2H), 7.40 (t, J=7.7 Hz, 1H), 7.49 (d, J=7.7 Hz, 1H), 7.73 (t, J=7.7 Hz, 1H), 7.82 (s, 1H), 8.02 (d, J=7.7 Hz, 1H), 12.55 (s, 1H); $^{13}$C NMR (175 MHz, DMSO-$d_6$) δ 13.9, 22.1, 25.0, 26.1, 29.1, 29.3, 31.0, 34.2, 38.5, 120.0, 125.5, 125.9, 126.0, 134.5, 148.4, 155.7, 161.3, 171.0; HRMS (ESI+) Calcd for $C_{18}H_{26}N_3O_2S$ [M+H]$^+$ 348.1740, found 348.1742 (Δ=−0.54 ppm).

Example 2. Assessment of the Affinity of Compounds for PEX-9 Binding

A blue shift in proMMP-9 tryptophan fluorescence was monitored to determine the binding affinity of all compounds. Binding of a test compound to MMP-9 was assayed by observing the change of tryptophan emission upon binding. Purified recombinant MMP-9 (50 nmol/L) or MMP-9/MMP-2PEX (50 nmol/L) was diluted in buffer (50 mmol/L Tris-HCl, 60 mmol/L KCl, and 0.05% Tween 20, pH 7.4) in the presence or absence of the test compound. As a control for protein stability and loss, an analogous buffer solution was added to the protein. The protein sample was excited at 280 nm and emission scans were collected from 290 to 400 nm, using slit widths of 0.3 nm on a QM 4/200SE spectrofluorimeter with double excitation and emission monochromators. Three emission scans were collected and averaged at each concentration. The $K_d$ was determined using the Prism software package (GraphPad V5) to fit the data to Equation (A).

$$\lambda_{max}=(\lambda_{max}^\infty \times [2])/(K_d+[2]) \qquad (A)$$

in which $\lambda_{max}$ is the wavelength at which maximal fluorescence of the protein was observed.

Results are summarized in Table 1. As Table 1 shows, the dissociation constant ($K_d$) for compound 3c binding to proMMP-9 is 0.32 μM, four times tighter than parent compound 1a. Moreover, a clear correlation between binding affinity and inhibition potency in the migration assay (see below) was observed. Thus, the biophysical SAR is maintained in the cellular assay and increased inhibition of cell migration is MMP9-dependent and due to optimization of chemical structure for binding the PEX-9 domain.

TABLE 1

PEX-9 Inhibitor Structures, Affinity to MMP9, and in vivo Efficacy of test compounds

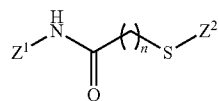

| Inhibitor | Z$^1$ | n | Z$^2$ | cLogP | Kd (μM) | % Inhibition of proMMP9-Mediated Migration at 50 μM |
|---|---|---|---|---|---|---|
| 1a | 4-difluoromethoxyphenyl | 1 | 4-oxo-6-propyl-1,4-dihydropyrimidin-2-yl | 3.1 ± 0.7 | 1.3 ± 0.3 | 51 ± 2 |
| 1b | phenyl | 1 | 4-oxo-6-propyl-1,4-dihydropyrimidin-2-yl | 3.0 ± 07 | 4.5 ± 0.6 | 12 ± 3 |
| 1c | 4-fluorophenyl | 1 | 4-oxo-6-propyl-1,4-dihydropyrimidin-2-yl | 3.3 ± 0.7 | 3.8 ± 0.6 | 29 ± 4 |
| 1d | benzimidazol-2-yl | 1 | 4-oxo-6-propyl-1,4-dihydropyrimidin-2-yl | 2.9 ± 0.7 | 1.2 ± 0.2 | 61 ± 2 |
| 1f | phenyl-(N-Me) | 1 | 4-oxo-6-propyl-1,4-dihydropyrimidin-2-yl | 2.2 ± 0.6 | N/A | 2 ± 6 |
| 2a | 4-difluoromethoxyphenyl | 3 | 4-oxo-6-propyl-1,4-dihydropyrimidin-2-yl | 4.0 ± 0.7 | 1.0 ± 0.2 | 63 ± 4 |

TABLE 1-continued

PEX-9 Inhibitor Structures, Affinity to MMP9, and in vivo Efficacy of test compounds $$Z^1\text{-}NH\text{-}C(=O)\text{-}(CH_2)_n\text{-}S\text{-}Z^2$$

| Inhibitor | $Z^1$ | n | $Z^2$ | cLogP | Kd (µM) | % Inhibition of proMMP9-Mediated Migration at 50 µM |
|---|---|---|---|---|---|---|
| 2c | 4-fluorophenyl | 3 | 4-oxo-6-propyl-1,4-dihydropyrimidin-2-yl | 3.7 ± 0.7 | 0.91 ± 0.1 | 68 ± 3 |
| 3a | 4-difluoromethoxyphenyl | 3 | 5,6,7,8-tetrahydro-4(1H)-quinazolinon-2-yl | 3.5 ± 0.7 | 0.6 ± 0.1 | 74 ± 2 |
| 3b | phenyl | 3 | 5,6,7,8-tetrahydro-4(1H)-quinazolinon-2-yl | 3.3 ± 0.6 | 0.5 ± 0.1 | 76 ± 1 |
| 3c | 4-fluorophenyl | 3 | 5,6,7,8-tetrahydro-4(1H)-quinazolinon-2-yl | 3.7 ± 0.7 | 0.32 ± 0.05 | 90 ± 2 |
| 3d | benzimidazol-2-yl | 3 | 5,6,7,8-tetrahydro-4(1H)-quinazolinon-2-yl | 3.2 ± 0.7 | 0.5 ± 0.2 | 77 ± 2 |
| 4a | 4-difluoromethoxyphenyl | 3 | 4-quinazolinon-2-yl | 3.3 ± 0.7 | 0.5 ± 0.1 | 78 ± 3 |
| 4b | phenyl | 3 | 4-quinazolinon-2-yl | 3.1 ± 0.6 | 0.8 ± 0.1 | 64 ± 4 |
| 4c | 4-fluorophenyl | 3 | 4-quinazolinon-2-yl | 3.5 ± 0.7 | 0.64 ± 0.06 | 73 ± 2 |
| 4d | benzimidazol-2-yl | 3 | 4-quinazolinon-2-yl | 3.1 ± 0.7 | 0.3 ± 0.1 | 81 ± 3 |
| 4e | n-hexyl | 3 | 4-quinazolinon-2-yl | 3.1 ± 0.7 | 0.9 ± 0.3 | 56 ± 1 |

Example 3. Assessment of the Inhibitory Activity of Test Compounds for proMMP9-Mediated Migration COS-1 cells were chosen for this set of experiments due to their low migratory capacity and complete lack of MMP-9 expression thereby minimizing potential artifacts when interpreting the data. Overexpression of proMMP-9 results in enhanced cell migration in a two-dimensional dot migration assay. This assay was initially used to test the efficacy of analogs at a single concentration, 50 µM. This concentration was used as a maximal cutoff because concentrations above 50 µM compound 1a did not increase inhibitor effectiveness in COS-1 cells.

Cells were mixed with type I collagen solution with or without compound, dotted onto a 96-well plate, and allowed to migrate for 18 hours. They were then fixed, stained and scored for extent of migration. 2-(4-Oxo-6-propyl-1,4-dihydropyrimidin-2-ylthio)-N(methyl)-phenylacetamide was used as a negative control. The results are summarized in Table 1 shown above.

Among the tested compounds, compound 3c was the most effective and was selected for further study. The migration assay was repeated in HT1080 fibrosarcoma cells, which endogenously express MMP-9, and the same inhibition potency was observed for the test compounds relative to control groups.

Example 4. PEX-9 Binding Specificity

A chimera of proMMP-9 and MMP-2 in which the MMP-9 PEX domain was replaced by that of MMP-2, (proMMP-9/MMP-2PEX) was tested for analog binding. Upon titration of compound 3c with the chimera, no shift in fluorescence was observed suggesting that 3c does not bind to MMP2-PEX.

As an additional test of binding selectivity, saturated transfer difference (STD) NMR was performed with purified recombinant proMMP-2 and proMMP-9 protein. ProMMP-2 and proMMP-9 are highly similar in structure and function, belonging to the same subfamily of MMPs known as the type IV collagenases and/or gelatinases. Thus proMMP-2 constitutes the best control for testing the selectivity of the PEX-9 inhibitor. Selective saturation of the 1.12 ppm resonance (proMMP-2 and proMMP-9) was used for STD NMR spectra. STD peaks were observed in the presence of proMMP-9, but not in the presence of proMMP-2, indicating that derivative compound 3c is specific for the PEX-9 target. Thus, binding specificity is maintained upon increasing binding affinity.

Example 5. PEX-9 Inhibitor Target Specificity

To test whether compound 3c is specific for inhibiting only proMMP9-mediated migration, a two-dimensional dot migration assay was performed using COS-1 cells engineered to stably express vector control pQCXIP, proMMP-2, proMMP-9, or proMMP-14 cDNA vectors. An immunoblot was performed to confirm protein expression and proper localization of each MMP (MMP-2/-9 are secreted while MMP-14 is membrane bound). As expected, expression of these three MMPs resulted in enhanced cellular migration in COS-1 cells. Treatment with either compound 1a or 3c only inhibited proMMP9-mediated migration: compound 3c was significantly more effective at inhibiting migration.

Example 6. Effect of PEX-9 Inhibitor on MMP-9 Catalytic Activity

Recombinant proMMP-9 protein was purified and incubated overnight in a 37° C. water bath in TNC buffer+1 mM APMA to artificially activate the protein. The next day, the purified protein was incubated with 10 μM fluorogenic peptide (Mca-Pro-Leu-Gly-Leu-Dpa-Ala-Arg-NH2), and catalytic activity was monitored over 2 hours in the presence of compounds 1a, 3c, 1f, and marimastat, a broad-spectrum MMP catalytic inhibitor. No inhibition of the catalytic activity was observed with 1a or 3c, corroborating that PEX-9 inhibitors do not modulate the catalytic activity of the protease. In the presence of marimastat ($K_d$=80 nM) no substrate cleavage was observed (Fig. 3D). Therefore, inhibition of proMMP9-mediated cell migration by compound 1a or 3c is not due to loss of proteolytic activity.

Example 7. Cell Viability Analysis

Compound 3c was evaluated for acute cytotoxicity. COS-1 cells stably expressing either vector control or proMMP-9 cDNA were treated with 50 μM 3c for 24 hours. As negative and positive controls, cells were treated with DMSO alone or 100 nM staurosporine (STS), an apoptosis inducer, respectively. Significant cell death was only observed after treatment with STS. A non-statistically significant 8% decrease in cell growth occurred after treatment with 50 μM of compound 3c. These experiments were repeated in endogenous MMP-9 expressing HT1080 fibrosarcoma cells, which were analyzed for chronic toxicity (cells were re-treated every three days for a total of nine days). No cell death was observed at 100 μM 3c.

Example 8. PEX-9 Inhibitors Decrease MMP-9 Dimer Formation and Association with EGFR Human fibroscarcoma HT1080 cells were co-transfected with MMP-9 cDNAs tagged with either a Myc or HA tag as previously reported. The next day, cells were switched to serum free media and treated with 50 μM of either compound 1a or 3c overnight. Using Myc antibody for immunoprecipitation and HA antibody for immunoblotting, the formation of dimeric MMP-9 was monitored. Compound 3c significantly blocked MMP-9 dimer formation as compared to control compound 1f. In addition, inhibition of PEX-9 with 1a or 3c reduced endogenous CD44 and EGFR co-immunoprecipitation. Moreover, these PEX-9 inhibitors reduced phosphorylation of $EGFR^{Tyr1068}$ and its downstream targets $AKT^{Ser473}$ and $Erk1/2^{Thr202/Tyr204}$.

Example 9. PEX-9 Inhibitors Disrupt MMP-9 Interaction with α4β1 Integrin

HT1080 cells transiently co-transfected with tagged MMP-9 cDNAs were prepared as described above. Inhibition of PEX-9 with 50 μM of either compound 1a or 3c reduced endogenous α4β1 integrin co-immunoprecipitation. Inhibition of PEX-9 with 50 μM of either compound 1a or 3c reduced $Src^{Tyr418}$ phosphorylation in addition to phosphorylation of Src downstream targets $FAK^{Tyr576/577}$ and $PAX^{Tyr118}$.

Example 10. Evaluation of MMP-9 Cell Surface Localization Upon Treatment with PEX-9 Inhibitors HT1080 cells were fixed in 4% paraformaldehyde then subsequently incubated with anti-MMP-9 in addition to anti-α4 and/or β1 integrin antibodies to monitor relative levels of localization of these proteins at the cell surface. The cells were counterstained with DAPI nuclear dye. Treatment with either compound 1a or 3c resulted in loss of MMP-9 from the cell surface. However, treatment with either solvent control DMSO or negative control compound 1f did not disrupt the localization of MMP-9 on the cell surface.

Example 11. Evaluation of Focal Adhesion Complexes in the Presence of PEX-9 Inhibitors HT1080 cells were fixed after overnight treatment with 50 μM PEX-9 inhibitors, probed for either $FAK^{Tyr576/577}$ or $PAX^{Tyr118}$ and counterstained with DAPI. A decrease in the formation of FAK and PAX adhesion junctions, normally depicted as "large punctae", was observed in cells after treatment with PEX-9 inhibitor compound 1a or 3c.

Example 12. Validation of MMP-9's Role in Signaling

MMP-9 expression was silenced using an shRNA approach as previously described. HT1080 cell lysates were collected and analyzed by immunoblot. Attenuation of MMP-9 expression resulted in a decrease in the phosphorylation of $EGFR^{Tyr1068}$, $FAK^{Tyr576/577}$, $PAX^{Tyr118}$, $Src^{Tyr418}$, $AKT^{Ser473}$, and $Erk1/2^{Thr202/Tyr204}$. These findings are corroborated by Kinexus antibody microarray screening of phosphorylation-dependent signaling pathways in MMP-9-transfected COS-1 cells in which Src, FAK, and PAX phosphorylation increase in proMMP-9 overexpressing cells.

Example 13. Treatment with PEX-9 Inhibitor Prevents Association of EGFR with CD44 and β1 Integrin HT1080 cells were treated with 50 μM 3c, 1a, 1f or DMSO alone. Cell lysates were collected and analyzed by a co-IP assay in which endogenous EGFR was captured with an anti-EGFR antibody and served as an input control. CD44 and R 1 integrin were individually probed on the immunoblot. Decreased interaction between EGFR-CD44 and EGFR-01 integrin was observed after treatment with 3c.

Example 14. Src Activation is a PEX-9 Dependent Process

Non-MMP-9 expressing MCF-7 breast cancer cells were transiently transfected with either vector control pcDNA3.1, proMMP-9, or chimeric proMMP-9/MMP-2PEX cDNA constructs. Phosphorylation of $Src^{Tyr418}$ was detected using an immunoblotting assay. Increased $Src^{Tyr418}$ phosphorylation was observed in proMMP-9 overexpressing cells. PEX domain swapping with MMP-2 has no effect on $Src^{Tyr418}$ phosphorylation similar to vector control pcDNA3.1 expressing cells.

Example 15. Effect of PEX-9 Inhibitors on Cell Adhesion

A 96-well plate was coated with a thin layer of either collagen or fibronectin (5 μg/ml in PBS) substrate before use. HT1080 cells were then seeded onto wells and incubated at 37° C. for 30 min in the presence of various inhibitors. Wells were washed and cells were fixed in 4% paraformaldehyde and stained with DAPI. Images of each 96-well were microscopically captured and counted for the number of cells still adherent to the coated surface using automated computer software. Compound 1a or 3c inhibited cellular adhesion whereas treatment with Marimastat, a broad-spectrum MMP catalytic inhibitor, had no observable effect on cell attachment. Solvent DMSO and compound 1f also had no affect on cell adhesion.

Example 16. Effect of Broad-Spectrum MMP Catalytic Inhibitor Marimastat on Focal Adhesion Complexes HT1080 cells treated with 80 nM of broad-spectrum MMP inhibitor marimastat were analyzed by immunofluorescence microscopy for both p-FAK$^{Tyr576/577}$ and p-PAX-$^{Tyr118}$. Treatment with marimastat did not prevent the formation of focal adhesion contact sites in HT1080 cells.

Example 17. Treatment with PEX-9 Inhibitor Prevents Both Angiogenesis and Invasion in a Chorioallantoic Membrane (CAM) Assay A CAM assay was carried out to evaluate angiogenic and invasive potential of HT1080 cells after treatment with 3c. HT1080 cells were adsorbed onto a gelatin sponge and implanted onto the surface of the chicken embryo CAM followed by treatment with 100 µM stock solution compound 1f, compound 1a or 3c (final drug concentration is estimated to be 0.5 µM). After a 4-day incubation, neovascularization was imaged and quantified. Treatment with either compound 1a or 3c significantly reduced the angiogenic potential of HT1080 cells as compared to solvent DMSO and negative compound 1f control treated cells.

HT1080 cells stably expressing GFP were mixed with a type I collagen solution (3 mg/mL) and seeded atop the CAM to ensure the cells localized to a specific area. Then they were treated with a 100 µM stock solution of compound 1f, compound 1a or 3c (final drug concentration is estimated to be 0.5 µM). The invasion of cancer cells through the epithelium and basement membrane of the upper CAM into connecting tissue was examined by hematoxylin and eosin staining in addition to fluorescence microscopy for GFP$^+$ cells. Treatment of HT1080 cells with either compound 1a or 3c reduced invasion of CAM tissue compared to treatment with either DMSO or compound 1f control.

Example 18. Additional MMP9X Inhibitors with Good Binding Affinity to MMP9 Based on the in Silico Screening The University of California San Francisco (UCSF) DOCK (6.7) algorithm was used to rank various structures for predicted binding affinity. See Alford, et al. "Targeting the Hemopexin-like Domain of Latent Matrix Metalloproteinase-9 (proMMP-9) with a Small Molecule Inhibitor Prevents the Formation of Focal Adhesion Junctions" *ACS Chemical Biology* 2017 12 (11), 2788-2803. The compounds (PEX-9 inhibitors) were DOCKed to the PEX-9 domain pocket (PDB Code 1ITV). This pocket is at the center of the four blades of the hemopexin domain. The docking analyses for the compounds shown in Table 1 was in good agreement with the observed $K_d$ values for the tested compounds. Moreover, as clearly shown in Table 1, there is a very good correlation between $K_d$ values and in vivo efficacy (inhibition of proMMP9-mediated migration). Therefore, the in silico screening of the new analogs of highly active compounds such as compounds 3c and 4d in Table 1 should have excellent predictability for their MMP9 affinities ($K_d$). Accordingly, we designed new analogs of 3c and 4d, as well as their "reverse amide" (wherein Y=—NHCOR$_1$) analogs and subjected them for the docking analysis using the same protocol as that used for the MMP9X inhibitors in Table 1. Selected compounds that exhibited good docking energy scores (larger negative values indicate higher affinity) are shown in Table 2 and Table 3. Table 2 shows variety of 3c and 4d analogs with good binding scores and Table 2 exhibits the "reverse amide" analogs of 3c and 4d, as well as their hybrids.

TABLE 2

Analogs of 3c and 4d with good docking energy scores (Formula I wherein Y = —CONHR$^1$)

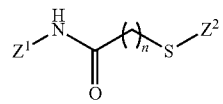

| Inhibitor | Z$^1$ | n | Z$^2$ | Docking energy score (Kcal/mol) | cLogP |
|---|---|---|---|---|---|
| 3c | 4-fluorophenyl | 3 | 5,6,7,8-tetrahydro-4(1H)-quinazolinon-2-yl | −8.0 | 3.7 |
| 3c-1 | 3-fluorophenyl | 3 | 5,6,7,8-tetrahydro-4(1H)-quinazolinon-2-yl | −7.6 | 3.8 |
| 3c-2 | 3-chlorophenyl | 3 | 5,6,7,8-tetrahydro-4(1H)-quinazolinon-2-yl | −7.4 | 4.00 |
| 3c-3 | 3-bromophenyl | 3 | 5,6,7,8-tetrahydro-4(1H)-quinazolinon-2-yl | −7.2 | 4.51 |
| 3c-4 | 3-hydroxyphenyl | 3 | 5,6,7,8-tetrahydro-4(1H)-quinazolinon-2-yl | −7.7 | 2.92 |
| 3c-5 | 3-difluoromethoxyphenyl | 3 | 5,6,7,8-tetrahydro-4(1H)-quinazolinon-2-yl | −7.7 | 3.62 |
| 3c-6 | 3-trifluoromethoxyphenyl | 3 | 5,6,7,8-tetrahydro-4(1H)-quinazolinon-2-yl | −7.6 | 4.48 |
| 3c-7 | 3-difluoromethylphenyl | 3 | 5,6,7,8-tetrahydro-4(1H)-quinazolinon-2-yl | −8.0 | 3.65 |
| 3c-8 | 3-trifluoromethylphenyl | 3 | 5,6,7,8-tetrahydro-4(1H)-quinazolinon-2-yl | -8.3 | 4.39 |
| 3c-9 | 4-chlorophenyl | 3 | 5,6,7,8-tetrahydro-4(1H)-quinazolinon-2-yl | −7.4 | 4.24 |

TABLE 2-continued

Analogs of 3c and 4d with good docking energy scores (Formula I wherein Y = —CONHR¹)

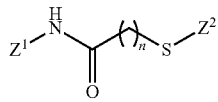

| Inhibitor | Z¹ | n | Z² | Docking energy score (Kcal/mol) | cLogP |
|---|---|---|---|---|---|
| 3c-10 | 4-bromophenyl | 3 | 5,6,7,8-tetrahydro-4(1H)-quinazolinon-2-yl | −7.2 | 4.48 |
| 3c-11 | 4-trifluoromethylphenyl | 3 | 5,6,7,8-tetrahydro-4(1H)-quinazolinon-2-yl | −7.7 | 4.71 |
| 3c-12 | 4-hydroxyphenyl | 3 | 5,6,7,8-tetrahydro-4(1H)-quinazolinon-2-yl | −7.5 | 2.53 |
| 3c-13 | 4-trifluoromethoxyphenyl | 3 | 5,6,7,8-tetrahydro-4(1H)-quinazolinon-2-yl | −7.8 | 4.32 |
| 3c-14 | 2,4-difluoromethylphenyl | 3 | 5,6,7,8-tetrahydro-4(1H)-quinazolinon-2-yl | −7.8 | 3.52 |
| 3c-15 | 3,5-difluoromethylphenyl | 3 | 5,6,7,8-tetrahydro-4(1H)-quinazolinon-2-yl | −7.5 | 4.37 |
| 3c-16 | 2,5-difluoromethylphenyl | 3 | 5,6,7,8-tetrahydro-4(1H)-quinazolinon-2-yl | −7.9 | 3.69 |
| 3c-17 | 3-trifluoromethyl-4-fluorophenyl | 3 | 5,6,7,8-tetrahydro-4(1H)-quinazolinon-2-yl | −8.4 | 4.81 |
| 3c-18 | 4-fluorophenyl | 3 | 6-oxo-5,6,7,8-tetrahydro-4(1H)-quinazolinon-2-yl | −8.1 | 2.40 |
| 3c-19 | 4-fluorophenyl | 3 | 7-oxo-5,6,7,8-tetrahydro-4(1H)-quinazolinon-2-yl | −8.1 | 2.40 |
| 4c | 4-fluorophenyl | 3 | 4-quinazolinon-2-yl | −7.9 | 3.20 |
| 4c-1 | 4-fluorophenyl | 3 | 5,7-dimethyl-4-quinazolinon-2-yl | −8.2 | 4.44 |
| 4c-2 | 4-fluorophenyl | 3 | 6-isopropyl-4-quinazolinon-2-yl | −8.1 | 4.86 |
| 4c-3 | 4-fluorophenyl | 3 | 6-dimethylamino-4-quinazolinon-2-yl | −7.7 | 3.63 |
| 4c-4 | 4-fluorophenyl | 3 | 5,6-difluoro-4-quinazolinon-2-yl | −7.9 | 3.54 |
| 4c-5 | 4-fluorophenyl | 3 | 7,8-difluoro-4-quinazolinon-2-yl | −8.1 | 3.54 |
| 4c-6 | 4-fluorophenyl | 3 | 5,7-difluoro-4-quinazolinon-2-yl | −8.1 | 3.66 |
| 4c-6 | 4-fluorophenyl | 3 | 6,8-difluoro-4-quinazolinon-2-yl | −7.8 | 3.66 |
| 4c-7 | 4-fluorophenyl | 3 | 3-methyl-6-fluoro-4-quinazolinon-2-yl | −7.9 | 3.34 |
| 4d | benzimidazol-2-yl | 3 | 4-quinazolinon-2-yl | −8.3 | 3.1 |
| 4d-1 | benzimidazol-2-yl | 3 | 6,7-difluoro-4-quinazolinon-2-yl | −8.2 | 3.08 |
| 4d-2 | 4,5,6,7-tetrahydro-benzimidazol-2-yl | 3 | 5,6-difluoro-4-quinazolinon-2-yl | −8.7 | 3.97 |
| 4d-3 | 5,7-difluorobenzimidazol-2-yl | 3 | quinazolinon-2-yl | −8.2 | 3.21 |
| 4d-4 | 5-amino-7-ethyl-benzimidazol-2-yl | 3 | quinazolinon-2-yl | −8.5 | 2.77 |
| 4d-5 | 6-acetyl-7-amino-benzimidazol-2-yl | 3 | quinazolinon-2-yl | −8.5 | 1.54 |
| 4d-6 | 6-hydroxy-7-fluoro-benzimidazol-2-yl | 3 | quinazolinon-2-yl | −8.7 | 2.78 |
| 4d-7 | 5-amino-7-acetamido-benzimidazol-2-yl | 3 | 5,6,7,8-tetrahydro-4(1H)-quinazolinon-2-yl | −8.3 | 0.92 |
| 4d-8 | 5,7-dihydroxy-benzimidazol-2-yl | 3 | 5,6,7,8-tetrahydro-4(1H)-quinazolinon-2-yl | −8.2 | 1.74 |
| 4d-9 | 5,6-diaminobenzimidazol-2-yl | 3 | quinazolinon-2-yl | −8.3 | 0.90 |
| 4d-10 | 5,6-diaminobenzimidazol-2-yl | 3 | 6,8-difluoroquinazolinon-2-yl | −8.4 | 1.04 |
| 4d-11 | benzimidazol-2-yl | 4 | quinazolinon-2-yl | −8.2 | 3.37 |
| 4d-12 | indol-2-yl | 3 | quinazolinon-2-yl | −8.3 | 3.73 |
| 4d-13 | 1-methylindol-2-yl | 3 | quinazolinon-2-yl | −7.8 | 4.13 |

TABLE 3

"Reverse amide" analogs of 3c, 4d and their hybrids with good docking energy scores
(Formula III, wherein Y = —NHCOR[1])

$$Z^1-\underset{H}{N}-\overset{O}{\underset{}{C}}-(CH_2)_n-S-Z^2$$

| Inhibitor | Z[1] | n | Z[2] | Docking energy score (Kcal/mol) | cLogP |
|---|---|---|---|---|---|
| IIIA-1 | 3-difluoromethylphenyl | 2 | 5,6,7,8-tetrahydro-4(1H)-quinazolinon-2-yl | −7.9 | 3.21 |
| IIIA-2 | 3-trifluoromethylphenyl | 2 | 5,6,7,8-tetrahydro-4(1H)-quinazolinon-2-yl | −8.4 | 3.89 |
| IIIA-3 | 3-difluoromethoxyphenyl | 2 | 5,6,7,8-tetrahydro-4(1H)-quinazolinon-2-yl | −8.0 | 2.65 |
| IIIA-4 | 3-trifluoromethoxyphenyl | 2 | 5,6,7,8-tetrahydro-4(1H)-quinazolinon-2-yl | −8.0 | 3.50 |
| IIIA-5 | 4-difluoromethylphenyl | 2 | 5,6,7,8-tetrahydro-4(1H)-quinazolinon-2-yl | −7.7 | 3.21 |
| IIIA-6 | 4-trifluoromethylphenyl | 2 | 5,6,7,8-tetrahydro-4(1H)-quinazolinon-2-yl | −8.1 | 3.80 |
| IIIA-7 | 4-difluoromethoxyphenyl | 2 | 5,6,7,8-tetrahydro-4(1H)-quinazolinon-2-yl | −8.3 | 3.18 |
| IIIA-8 | 4-trifluoromethoxyphenyl | 2 | 5,6,7,8-tetrahydro-4(1H)-quinazolinon-2-yl | −8.6 | 4.03 |
| IIIA-9 | 4-methoxyphenyl | 2 | 5,6,7,8-tetrahydro-4(1H)-quinazolinon-2-yl | −7.7 | 3.00 |
| IIIA-10 | 4-fluorophenyl | 2 | 5,6,7,8-tetrahydro-4(1H)-quinazolinon-2-yl | −7.9 | 3.56 |
| IIIA-11 | 3-difluoromethylphenyl | 3 | 5,6,7,8-tetrahydro-4(1H)-quinazolinon-2-yl | −8.2 | 3.42 |
| IIIA-12 | 3-trifluoromethylphenyl | 3 | 5,6,7,8-tetrahydro-4(1H)-quinazolinon-2-yl | −8.3 | 4.11 |
| IIIA-11 | 3-difluoromethoxyphenyl | 3 | 5,6,7,8-tetrahydro-4(1H)-quinazolinon-2-yl | −8.1 | 2.86 |
| IIIA-12 | 3-trifluoromethoxyphenyl | 3 | 5,6,7,8-tetrahydro-4(1H)-quinazolinon-2-yl | −8.1 | 3.72 |
| IIIA-13 | 4-difluoromethylphenyl | 3 | 5,6,7,8-tetrahydro-4(1H)-quinazolinon-2-yl | −7.8 | 3.42 |
| IIIA-14 | 4-trifluoromethylphenyl | 3 | 5,6,7,8-tetrahydro-4(1H)-quinazolinon-2-yl | −7.9 | 4.02 |
| IIIA-15 | 4-difluoromethoxyphenyl | 3 | 5,6,7,8-tetrahydro-4(1H)-quinazolinon-2-yl | −8.1 | 3.40 |
| IIIA-16 | 4-trifluoromethoxyphenyl | 3 | 5,6,7,8-tetrahydro-4(1H)-quinazolinon-2-yl | −8.1 | 4.25 |
| IIIA-17 | 4-methoxyphenyl | 3 | 5,6,7,8-tetrahydro-4(1H)-quinazolinon-2-yl | −7.7 | 3.22 |
| IIIB-1 | benzimidazol-2-yl | 2 | quinazolinon-2-yl | −8.5 | 3.06 |
| IIIB-2 | 4,5,6,7-terahydro-benzimidazol-2-yl | 2 | quinazolinon-2-yl | −8.4 | 3.96 |
| IIIB-3 | 4,5,6,7-tetrahydro-benzimidazol-2-yl | 3 | 5,6-difluoroquinazolinon-2-yl | −8.7 | 3.97 |
| IIIB-4 | 4,5,6,7-terahydro-benzimidazol-2-yl | 2 | 6,7-difluoroquinazolinon-2-yl | −8.7 | 3.97 |
| IIIB-5 | 4,5,6,7-terahydro-benzimidazol-2-yl | 2 | 5,8-difluoroquinazolinon-2-yl | −8.3 | 4.13 |
| IIIB-6 | 4,5,6,7-terahydro-benzimidazol-2-yl | 2 | 6,8-difluoroquinazolinon-2-yl | −7.6 | 4.10 |
| IIIB-7 | benzimidazol-2-yl | 2 | 6,8-difluoroquinazolinon-2-yl | −8.0 | 2.99 |
| IIIB-8 | 6-difluoromethyl-benzimidazol-2-yl | 2 | quinazolinon-2-yl | −9.1 | 3.22 |
| IIIB-9 | 6-trifluoromethyl-benzimidazol-2-yl | 2 | quinazolinon-2-yl | −9.0 | 3.42 |
| IIIB-10 | benzimidazol-2-yl | 3 | quinazolinon-2-yl | −8.4 | 3.06 |
| IIIB-11 | 4,5,6,7-terahydro-benzimidazol-2-yl | 3 | quinazolinon-2-yl | −8.3 | 4.17 |
| IIIB-12 | benzimidazol-2-yl | 3 | 6,7-difluoro-4-quinazolinon-2-yl | −8.1 | 3.08 |
| IIIB-13 | benzimidazol-2-yl | 3 | 6,8-difluoro-4-quinazolinon-2-yl | −8.8 | 3.21 |
| IIIB-14 | 6-difluoromethyl-benzimidazol-2-yl | 3 | quinazolinon-2-yl | −8.9 | 3.44 |
| IIIB-15 | 6-trifluoromethyl-benzimidazol-2-yl | 3 | quinazolinon-2-yl | −9.0 | 3.64 |

The invention claimed is:
1. A compound of Formula II:

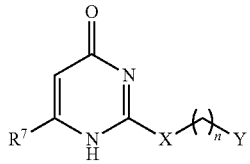

or a pharmaceutically acceptable salt, stereoisomer, or tautomer thereof,
wherein:
Y is C(O)NHR$^1$;
R$^1$ is alkyl, cycloalkyl, or aryl;
  wherein the alkyl is a linear or branched, saturated or unsaturated carbon chain having 1 to 18 carbon atoms;
  wherein the alkyl is optionally substituted with one or more substituents independently selected from the group consisting of F, Cl, Br, I, NH$_2$, NHR$^4$, NHC(O)R$^4$, NHC(O)OR$^4$, NR$^5$R$^6$, OH, OR$^4$, SR$^4$, S(O)R$^4$, S(O)$_2$R$^4$, cycloalkyl, and aryl;
  wherein the cycloalkyl is a fused or unfused, carbocyclic or heterocyclic non-aromatic ring system having 5 to 16 ring members;
  wherein the cycloalkyl is optionally substituted with one or more substituents independently selected from the group consisting of F, Cl, Br, I, alkyl, NH$_2$, NHR$^4$, NHC(O)R$^4$, NHC(O)OR$^4$, NR$^5$R$^6$, OH, OR$^4$, =O, SR$^4$, cycloalkyl, and aryl;
  wherein the aryl is carbocyclic or heterocyclic;
  wherein the carbocyclic aryl is a fused or unfused ring system having 6 to 16 ring members;
  wherein the carbocyclic aryl is optionally substituted with one or more substituents independently selected from the group consisting of F, Cl, Br, I, CN, NO$_2$, alkyl, C(O)R$^4$, C(O)NHR$^4$, C(O)NR$^5$R$^6$, C(O)OH, C(O)OR$^4$, NH$_2$, NHR$^4$, NHC(O)OR$^4$, NR$^5$R$^6$, OH, OR$^4$, SR$^4$, cycloalkyl, and aryl;
  wherein the heterocyclic aryl is a fused or unfused ring system having 5 to 16 ring members;
  wherein the heterocyclic aryl contains at least one heteroatom or heteroatomic group independently selected from the group consisting of N, NH, O, and S; and
  wherein the heterocyclic aryl is optionally substituted with one or more substituents selected from the group consisting of F, Cl, Br, I, CN, NO$_2$, alkyl, C(O)R$^4$, C(O)NHR$^4$, C(O)NR$^5$R$^6$, C(O)OH, C(O)OR$^4$, NH$_2$, NHR$^4$, NHC(O)OR$^4$, NR$^5$R$^6$, OH, OR$^4$, SR$^4$, cycloalkyl, and aryl;
X is —NH—, —NR$^3$—, —O—, or —S—;
R$^3$ is C$_{1-5}$ alkyl;
  wherein the C$_{1-5}$ alkyl is linear or branched and saturated or unsaturated; and
  wherein the C$_{1-5}$ alkyl is optionally substituted with one or more substituents independently selected from the group consisting of F, Cl, Br, I, NH$_2$, NHR$^4$, NHC(O)R$^4$, NHC(O)OR$^4$, NR$^5$R$^6$, OH, OR$^4$, SR$^4$, S(O)R$^4$, S(O)$_2$R$^4$, cycloalkyl, and aryl;
each R$^4$ is independently alkyl, cycloalkyl, or aryl;
  wherein each alkyl is independently a linear or branched, saturated or unsaturated carbon chain having 1 to 18 carbon atoms;
  wherein each alkyl is optionally and independently substituted with one or more substituents independently selected from the group consisting of F, Cl, Br, I, NH$_2$, NH(alkyl), NH(cycloalkyl), NH(aryl), NHC(O)alkyl, NHC(O)cycloalkyl, NHC(O)aryl, NHC(O)Oalkyl, NHC(O)Ocycloalkyl, NHC(O)Oaryl, NR$^5$R$^6$, OH, O(alkyl), O(cycloalkyl), O(aryl), S(alkyl), S(cycloalkyl), S(aryl), S(O)alkyl, S(O)cycloalkyl, S(O)aryl, S(O)$_2$alkyl, S(O)$_2$cycloalkyl, S(O)$_2$aryl, cycloalkyl, and aryl;
  wherein each cycloalkyl is independently a fused or unfused, carbocyclic or heterocyclic non-aromatic ring system having 5 to 16 ring members;
  wherein each cycloalkyl is optionally and independently substituted with one or more substituents independently selected from the group consisting of F, Cl, Br, I, NH$_2$, NH(alkyl), NH(cycloalkyl), NH(aryl), NHC(O)alkyl, NHC(O)cycloalkyl, NHC(O)aryl, NHC(O)Oalkyl, NHC(O)Ocycloalkyl, NHC(O)Oaryl, NR$^5$R$^6$, OH, O(alkyl), O(cycloalkyl), O(aryl), S(alkyl), S(cycloalkyl), S(aryl), S(O)alkyl, S(O)cycloalkyl, S(O)aryl, S(O)$_2$alkyl, S(O)$_2$cycloalkyl, S(O)$_2$aryl, cycloalkyl, and aryl;
  wherein each aryl is independently carbocyclic or heterocyclic;
  wherein each carbocyclic aryl is independently a fused or unfused ring system having 6 to 16 ring members;
  wherein each carbocyclic aryl is optionally and independently substituted with one or more substituents independently selected from the group consisting of F, Cl, Br, I, NH$_2$, NH(alkyl), NH(cycloalkyl), NH(aryl), NHC(O)alkyl, NHC(O)cycloalkyl, NHC(O)aryl, NHC(O)Oalkyl, NHC(O)Ocycloalkyl, NHC(O)Oaryl, NR$^5$R$^6$, OH, O(alkyl), O(cycloalkyl), O(aryl), S(alkyl), S(cycloalkyl), S(aryl), S(O) alkyl, S(O)cycloalkyl, S(O)aryl, S(O)$_2$alkyl, S(O)$_2$cycloalkyl, S(O)$_2$aryl, cycloalkyl, and aryl;
  wherein each heterocyclic aryl is independently a fused or unfused ring system having 5 to 16 ring members;
  wherein each heterocyclic aryl independently contains at least one heteroatom or heteroatomic group independently selected from the group consisting of N, NH, O, and S; and
  wherein each heterocyclic aryl is optionally and independently substituted with one or more substituents independently selected from the group consisting of F, Cl, Br, I, alkyl, NH$_2$, NH(alkyl), NH(cycloalkyl), NH(aryl), NHC(O)alkyl, NHC(O)cycloalkyl, NHC(O)aryl, NHC(O)Oalkyl, NHC(O)Ocycloalkyl, NHC(O)Oaryl, NR$^5$R$^6$, OH, O(alkyl), O(cycloalkyl), O(aryl), S(alkyl), S(cycloalkyl), S(aryl), S(O)alkyl, S(O)cycloalkyl, S(O)aryl, S(O)$_2$alkyl, S(O)$_2$cycloalkyl, S(O)$_2$aryl, cycloalkyl, and aryl;
each R$^5$ is independently alkyl, cycloalkyl, or aryl;
  wherein each alkyl is independently a linear or branched, saturated or unsaturated carbon chain having 1 to 18 carbon atoms;
  wherein each alkyl is optionally and independently substituted with one or more substituents independently selected from the group consisting of F, Cl, Br, I, $NH_2$, NH(alkyl), NH(cycloalkyl), NH(aryl), NHC(O)alkyl, NHC(O)cycloalkyl, NHC(O)aryl, NHC(O)Oalkyl, NHC(O)Ocycloalkyl, NHC(O)Oaryl, $NR^5R^6$, OH, O(alkyl), O(cycloalkyl), O(aryl), S(alkyl), S(cycloalkyl), S(aryl), S(O)alkyl, S(O)cycloalkyl, S(O)aryl, $S(O)_2$alkyl, $S(O)_2$cycloalkyl, $S(O)_2$aryl, cycloalkyl, and aryl;

wherein each cycloalkyl is independently a fused or unfused, carbocyclic or heterocyclic non-aromatic ring system having 5 to 16 ring members;

wherein each cycloalkyl is optionally and independently substituted with one or more substituents independently selected from the group consisting of F, Cl, Br, I, $NH_2$, NH(alkyl), NH(cycloalkyl), NH(aryl), NHC(O)alkyl, NHC(O)cycloalkyl, NHC(O)aryl, NHC(O)Oalkyl, NHC(O)Ocycloalkyl, NHC(O)Oaryl, $NR^5R^6$, OH, O(alkyl), O(cycloalkyl), O(aryl), S(alkyl), S(cycloalkyl), S(aryl), S(O)alkyl, S(O)cycloalkyl, S(O)aryl, $S(O)_2$alkyl, $S(O)_2$cycloalkyl, $S(O)_2$aryl, cycloalkyl, and aryl;

wherein each aryl is independently carbocyclic or heterocyclic;

wherein each carbocyclic aryl is independently a fused or unfused ring system having 6 to 16 ring members;

wherein each carbocyclic aryl is optionally and independently substituted with one or more substituents independently selected from the group consisting of F, Cl, Br, I, $NH_2$, NH(alkyl), NH(cycloalkyl), NH(aryl), NHC(O)alkyl, NHC(O)cycloalkyl, NHC(O)aryl, NHC(O)Oalkyl, NHC(O)Ocycloalkyl, NHC(O)Oaryl, $NR^5R^6$, OH, O(alkyl), O(cycloalkyl), O(aryl), S(alkyl), S(cycloalkyl), S(aryl), S(O)alkyl, S(O)cycloalkyl, S(O)aryl, $S(O)_2$alkyl, $S(O)_2$cycloalkyl, $S(O)_2$aryl, cycloalkyl, and aryl;

wherein each heterocyclic aryl is independently a fused or unfused ring system having 5 to 16 ring members;

wherein each heterocyclic aryl independently contains at least one heteroatom or heteroatomic group independently selected from the group consisting of N, NH, O, and S; and wherein each heterocyclic aryl is optionally and independently substituted with one or more substituents independently selected from the group consisting of F, Cl, Br, I, alkyl, $NH_2$, NH(alkyl), NH(cycloalkyl), NH(aryl), NHC(O)alkyl, NHC(O)cycloalkyl, NHC(O)aryl, NHC(O)Oalkyl, NHC(O)Ocycloalkyl, NHC(O)Oaryl, $NR^5R^6$, OH, O(alkyl), O(cycloalkyl), O(aryl), S(alkyl), S(cycloalkyl), S(aryl), S(O)alkyl, S(O)cycloalkyl, S(O)aryl, $S(O)_2$alkyl, $S(O)_2$cycloalkyl, $S(O)_2$aryl, cycloalkyl, and aryl;

each $R^6$ is independently alkyl, cycloalkyl, or aryl;

wherein each alkyl is independently a linear or branched, saturated or unsaturated carbon chain having 1 to 18 carbon atoms;

wherein each alkyl is optionally and independently substituted with one or more substituents independently selected from the group consisting of F, Cl, Br, I, $NH_2$, NH(alkyl), NH(cycloalkyl), NH(aryl), NHC(O)alkyl, NHC(O)cycloalkyl, NHC(O)aryl, NHC(O)Oalkyl, NHC(O)Ocycloalkyl, NHC(O)Oaryl, $NR^5R^6$, OH, O(alkyl), O(cycloalkyl), O(aryl), S(alkyl), S(cycloalkyl), S(aryl), S(O)alkyl, S(O)cycloalkyl, S(O)aryl, $S(O)_2$alkyl, $S(O)_2$cycloalkyl, $S(O)_2$aryl, cycloalkyl, and aryl;

wherein each cycloalkyl is independently a fused or unfused, carbocyclic or heterocyclic non-aromatic ring system having 5 to 16 ring members;

wherein each cycloalkyl is optionally and independently substituted with one or more substituents independently selected from the group consisting of F, Cl, Br, I, $NH_2$, NH(alkyl), NH(cycloalkyl), NH(aryl), NHC(O)alkyl, NHC(O)cycloalkyl, NHC(O)aryl, NHC(O)Oalkyl, NHC(O)Ocycloalkyl, NHC(O)Oaryl, $NR^5R^6$, OH, O(alkyl), O(cycloalkyl), O(aryl), S(alkyl), S(cycloalkyl), S(aryl), S(O)alkyl, S(O)cycloalkyl, S(O)aryl, $S(O)_2$alkyl, $S(O)_2$cycloalkyl, $S(O)_2$aryl, cycloalkyl, and aryl;

wherein each aryl is independently carbocyclic or heterocyclic;

wherein each carbocyclic aryl is independently a fused or unfused ring system having 6 to 16 ring members;

wherein each carbocyclic aryl is optionally and independently substituted with one or more substituents independently selected from the group consisting of F, Cl, Br, I, $NH_2$, NH(alkyl), NH(cycloalkyl), NH(aryl), NHC(O)alkyl, NHC(O)cycloalkyl, NHC(O)aryl, NHC(O)Oalkyl, NHC(O)Ocycloalkyl, NHC(O)Oaryl, $NR^5R^6$, OH, O(alkyl), O(cycloalkyl), O(aryl), S(alkyl), S(cycloalkyl), S(aryl), S(O)alkyl, S(O)cycloalkyl, S(O)aryl, $S(O)_2$alkyl, $S(O)_2$cycloalkyl, $S(O)_2$aryl, cycloalkyl, and aryl;

wherein each heterocyclic aryl is independently a fused or unfused ring system having 5 to 16 ring members;

wherein each heterocyclic aryl independently contains at least one heteroatom or heteroatomic group independently selected from the group consisting of N, NH, O, and S; and wherein each heterocyclic aryl is optionally and independently substituted with one or more substituents independently selected from the group consisting of F, Cl, Br, I, alkyl, $NH_2$, NH(alkyl), NH(cycloalkyl), NH(aryl), NHC(O)alkyl, NHC(O)cycloalkyl, NHC(O)aryl, NHC(O)Oalkyl, NHC(O)Ocycloalkyl, NHC(O)Oaryl, $NR^5R^6$, OH, O(alkyl), O(cycloalkyl), O(aryl), S(alkyl), S(cycloalkyl), S(aryl), S(O)alkyl, S(O)cycloalkyl, S(O)aryl, $S(O)_2$alkyl, $S(O)_2$cycloalkyl, $S(O)_2$aryl, cycloalkyl, and aryl; or each $R^5$ and $R^6$, together with the nitrogen atom to which they are attached, independently forms an unsubstituted heterocyclic alkyl or an unsubstituted heterocyclic aryl;

wherein each heterocyclic alkyl independently contains at least one heteroatom independently selected from the group consisting of nitrogen, oxygen and sulfur;

wherein each heterocyclic alkyl is optionally and independently substituted with one or more substituents independently selected from the group consisting of F, Cl, Br, I, $NH_2$, NH(alkyl), NH(cycloalkyl), NH(aryl), NHC(O)alkyl, NHC(O)cycloalkyl, NHC(O)aryl, NHC(O)Oalkyl, NHC(O)Ocycloalkyl, NHC(O)Oaryl, $NR^5R^6$, OH, O(alkyl), O(cycloalkyl), O(aryl), S(alkyl), S (cycloalkyl), S(aryl), S(O)alkyl, S(O)cycloalkyl, S(O)aryl, S(O)₂alkyl, S(O)₂cycloalkyl, S(O)₂aryl, cycloalkyl, and aryl;
- wherein each heterocyclic aryl is independently a fused or unfused ring system having 5 to 16 ring members;
- wherein each heterocyclic aryl independently contains at least one heteroatom or heteroatomic group independently selected from the group consisting of N, NH, O, and S; and
- wherein each heterocyclic aryl is optionally and independently substituted with one or more substituents independently selected from the group consisting of F, Cl, Br, I, NH₂, NH(alkyl), NH(cycloalkyl), NH(aryl), NHC(O)alkyl, NHC(O)cycloalkyl, NHC(O)aryl, NHC(O)Oalkyl, NHC(O)Ocycloalkyl, NHC(O)Oaryl, NR⁵R⁶, OH, O(alkyl), O(cycloalkyl), O(aryl), S(alkyl), S(cycloalkyl), S(aryl), S(O)alkyl, S(O)cycloalkyl, S(O)aryl, S(O)₂alkyl, S(O)₂cycloalkyl, S(O)₂aryl, cycloalkyl, and aryl;

R⁷ is C₁₋₆ alkyl;
- wherein the C₁₋₆ alkyl is linear or branched and saturated or unsaturated; and
- wherein the C₁₋₆ alkyl is optionally substituted with one or more substituents independently selected from the group consisting of F, Cl, Br, I, NH₂, NHR⁴, NHC(O)R⁴, NHC(O)OR⁴, NR⁵R⁶, OH, OR⁴, SR⁴, S(O)R⁴, S(O)₂R⁴, cycloalkyl, and aryl; and n is 2, 3, or 4;
with the proviso that if Y is C(O)NHR¹, then n is not 2.

2. The compound according to claim 1, wherein the compound is selected from the group consisting of:

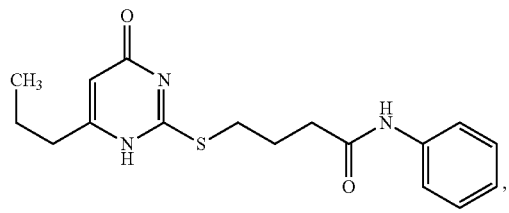
,

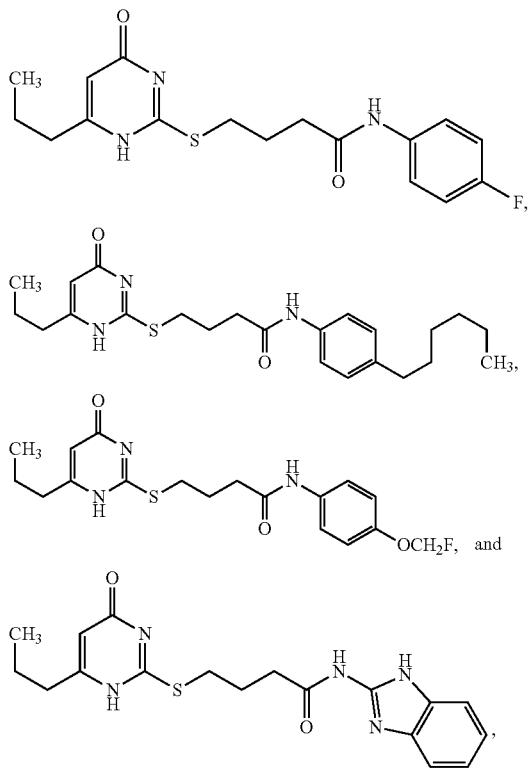

or a pharmaceutically acceptable salt or tautomer thereof.

3. A method for inhibiting matrix metalloproteinase-9 (MMP-9) hemopexin domain activity in a patient in need thereof, wherein the method comprises administering to the patient a therapeutically effective amount of a compound according to claim 1, or a pharmaceutically acceptable salt, stereoisomer, or tautomer thereof.

4. The method of claim 3, wherein the patient has cancer.

5. The method of claim 4, wherein the cancer is chronic lymphocytic leukemia or refractory lymphoma.

* * * * *

UNITED STATES PATENT AND TRADEMARK OFFICE
CERTIFICATE OF CORRECTION

PATENT NO. : 12,018,003 B2
APPLICATION NO. : 17/353075
DATED : June 25, 2024
INVENTOR(S) : Iwao Ojima et al.

It is certified that error appears in the above-identified patent and that said Letters Patent is hereby corrected as shown below:

In the Specification

Column 2, Line 58:
Now reads: "the proviso that n 2"
Should read: --the proviso that n≠2--

Column 5, Line 37:
Now reads: "indan-1-yl, indqn-2-yl"
Should read: --indan-1-yl, indan-2-yl--

Column 5, Line 38:
Now reads: "bicycico"
Should read: --bicyclo--

Column 28, Line 20 and 22:
Now reads: "DMSO-d6"
Should read: --DMSO-$d_6$--

Column 28, Line 24:
Now reads: "C8H11N2OS"
Should read: --$C_8H_{11}N_2OS$--

Column 29, Line 66:
Now reads: "washed with (50 mL)"
Should read: --washed with water (50 ml)--

Column 32, chart:
Now reads: "3.0 ± 07"
Should read: --3.0 ± 0.7--

Signed and Sealed this
Thirtieth Day of September, 2025

John A. Squires
*Director of the United States Patent and Trademark Office*

CERTIFICATE OF CORRECTION (continued)
U.S. Pat. No. 12,018,003 B2

Column 36, Line 37:
Now reads: "and R1 integrin:"
Should read: --and β1 integrin--

Column 36, Line 39:
Now reads: "EGFR-01 integrin"
Should read: --EGFR-β1 integrin--

Column 41, chart III B-2, III B-4, IIIB-5, III B-6, III B-11:
Now reads: "4,5,6,7-terahydrobenzimidazol-2-yl"
Should read: --4,5,6,7-tetrahydrobenzimidazol-2-yl--